US005789558A

United States Patent [19]
Casey et al.

[11] Patent Number: 5,789,558
[45] Date of Patent: Aug. 4, 1998

[54] PROTEIN PRENYLTRANSFERASE

[75] Inventors: Patrick J. Casey; Fang Zhang, both of Durham, N.C.; Ronald E. Diehl, Line Lexington, Pa.; Nancy E. Kohl, Wyndmoor, Pa.; Charles A. Omer, Lansdale, Pa.

[73] Assignees: Merck & Co., Inc., Rahway, N.J.; Duke University, Durham, N.C.

[21] Appl. No.: 188,277

[22] Filed: Jan. 31, 1994

[51] Int. Cl.⁶ .............................. C12N 9/10; C12N 15/54
[52] U.S. Cl. .................. 536/23.2; 435/193; 435/320.1
[58] Field of Search ......................... 435/69.1, 320.1, 435/193, 252.3, 254.11; 536/23.2; 935/24, 55

[56] References Cited

PUBLICATIONS

FASEB J. 7:A1042 (1993).
Lee, C. C. et al. *Science* 239:1288–1291 (1988).
Zhang, F.L. et al. *J.Biol.Chem.* 269(5):3175–3180 (1994).

*Primary Examiner*—Dian C. Jacobson
*Attorney, Agent, or Firm*—David A. Muthard; Mark R. Daniel

[57] ABSTRACT

The present invention relates, in general, to a protein prenyltransferase and, in particular, to protein geranylgeranyltransferase (GGTase-I) and to a nucleic acid sequence encoding same. The invention also relates to methods of producing GGTase-I and geranylgeranyl modified polypeptides. The invention further relates to a method of screening compounds for the ability to alter GGTase-I activity.

3 Claims, 8 Drawing Sheets

Fig. 1

Rat GGTase-I β subunit, cDNA and deduced protein sequence

```
       GGACAGGCCATGGCGGCCAC AGAGGATGACAGACTGGGCGG AGAGGGAGAAGGAGAACGG   60
                  M  A  A  T   E  D  D  R  L  A  G   S  G  E  G  E  R

1    CTGGATTCCTGCGGGACCG ACACGTGCGGTTCTTCCAGC GCTGCCTTCCAGTCTTGCCG  120
        L  D  F  L  R  D  R   H  V  R  F  F  Q  R   C  L  Q  V  L  P

18    GAGCGGGTATTCTTCGCTGGA GACCAGGCAGCTGACAATTG CATTTTTGCACTCTCTGGG  180
        E  R  Y  S  S  L  E   T  S  R  L  T  I  A   F  F  A  L  S  G

38    CTGGATATGTTGGACTCCTT GGATGTGGGTGAACAAAGACG ATATAATAGAGTGGATTTAT  240
        L  D  M  L  D  S  L   D  V  V  N  K  D  D   I  I  E  W  I  Y

58    TCCTTGCAGGTTCTTCCCAC AGAAGACAGTCAAATCTGG ATCGCTGTGGTTTCCGAGGT  300
        S  L  Q  V  L  P  T   E  D  R  S  N  L  D   R  C  G  F  R  G

78    TCTTCATATTTGGGTATTCC ATTCAACCCATCAAAGAATC CAGGCACAGCTCATCCTTAT  360
        S  S  Y  L  G  I  P   F  N  P  S  K  N  P   G  T  A  H  P  Y

98    GACAGTGGACACATAGCGAT GACTTACACTGGTCTTTCCT GTTTAATTATTCTTGGAGAT  420
        D  S  G  H  I  A  M   T  Y  T  G  L  S  C   L  I  I  L  G  D

118    GATTTAAGCCGAGTAGATAA AGAAGCTTGCTTAGCAGGCT TGAGAGCACTTCAGCTGGAA  480
        D  L  S  R  V  D  K   E  A  C  L  A  G  L   R  A  L  Q  L  E

138    GATGGGAGCTTCTGTGCTGT TCCTGAAGGCAGTGAGAATG ACATGAGGTTTGTGTACTGT  540
        D  G  S  F  C  A  V   P  E  G  S  E  N  D   M  R  F  V  Y  C

158    GCTTCCTGCATTTGCTATAT GCTCAACAACTGGTCAGGCA TGGATATGAAGAAAGCCATC  600
        A  S  C  I  C  Y  M   L  N  N  W  S  G  M   D  M  K  K  A  I

178    AGCTACATTAGAAGAAGTAT GTCCTATGACAATGGCCTGG CACAGGGGCAGGACTTGAG  660
        S  Y  I  R  R  S  M   S  Y  D  N  G  L  A   Q  G  A  G  L  E

```
        TCTCATGGAGGATCCACCTT TTGTGGCATTGCGTCACTGT GCCTGATGGGTAAACTGGAA  720
        S   H   G   G   S   T   F   C   G   I   A   S   L   C   L   M   G   K   L   E
        GAAGTTTTTCAGAGAAAGA ACTGAACCGGATAAAGAGGT GGTGCATAATGAGGCAGCAG   780
218     E   V   F   S   E   K   E   L   N   R   I   K   R   W   C   I   M   R   Q   Q
        AACGGGTACCACGGAAGACC TAACAAGCCTGTCGACACCT GTTACTCTTTCTGGGTGGGA   840
238     N   G   Y   H   G   R   P   N   K   P   V   D   T   C   Y   S   F   W   V   G
        GCAACACTAAAGCTTTTTGAA AATTTCCAGTACACTAACT TTGAGAAGAATAGGAATTAC   900
258     A   T   L   K   L   L   K   I   F   Q   Y   T   N   F   E   K   N   R   N   Y
        ATCTTATCAACTCAGGATCG CCTTGTTGGGGATTTGCTA AATGGCCAGACAGTCATCCA   960
278     I   L   S   T   Q   D   R   L   V   G   G   F   A   K   W   P   D   S   H   P
        GATGCTTTGCATGCTACTT CGGGATCTGTGGCCCTGTCAC TAATGGAGGAGAGTGGAATT  1020
298     D   A   L   H   A   Y   F   G   I   C   G   L   S   L   M   E   E   S   G   I
        TGTAAAGTTCATCCTGCTCT GAATGTAAGCACACGAACTT CTGAGCGCCTCCGAGATCTC  1080
318     C   K   V   H   P   A   L   N   V   S   T   R   T   S   E   R   L   R   D   L
        CATCAAAGCTGGAAGACCAA GGACTCTAAACAGTGCTCAG ACAATGTCCATATTCCAGT   1140
338     H   Q   S   W   K   T   K   D   S   K   Q   C   S   D   N   V   H   I   S
        TGACTAACCCTGGGGTAAAG GGTGTGTAGCATACGTGTAG CTCAAGGTTAAAAGCCATGT  1200
358     
        GTAACCAAGTGTGCTCTTCT TTAAGGGTTAGTCGTAAAAG TCAGAAGCGTGTACTGCTAG  1260
        TCTTCAGGATATATGCTCTTA GGCCAGTGACCACTGTCATG GATTTCAAGAAAATCCTTGT  1320
        TGACGTGTGGACATCAGCAG AACTCTGGTATGGTTCTTAA CTGTTACACTGTGTTTCTGA  1380
        GACCTTTCATGGGCAGATA TGTTTGTAGGTTATCTTCTT AAAACCCTCAGTACAAGTTC  1440
        TGGCTTACAAAAATGTACGTA AACCTTCAAAACAAGTTTAC ACTCCATATGCATTGATAA  1500
        TCTTCAGGTGAGCATTTAAC GATCACTTAAAAATCGCTAC TGCTGATGGGAAGAAATTTG  1560
        TTTATCCG  1568
```

Fig. 2

```
   1 GAATAAAATGAACAATTCAGTTCCTCAGTCACATGAGCTGTGTGTCAAATGCACAACAGC
  61 CGTATGTGGCTCGTGGCCCCTGTACCGGACACTCCCATCCCTGCAGAGTTACTGGACAGT
 121 GCTGATCTAGGGATTCTGTTACAAAATCCATGAAAGTGTTCAGCACAATGCCGGCCCAT
 181 ATAAACGTCAGTAGTTGTTGTTATTATAATTAGTCTTGACCCAACGGCAAATTCACTTTG
 241 AGACCTTAGATAAATCACTCTACCTCTCTGAGCCTGGTTTCCTTGCCCTAAAAGGATGGC
 301 AAGGGGCTGGGCATGGTGGCCACTGAGGATGAGAGGCTAGCAGGGAGCGGTGAGGGAGAG
                   M  V  A  T  E  D  E  R  L  A  G  S  G  E  G  E   16
 361 CGGCTGGATTTCTTACGGGATCGGCACGTGCGATTTTTCCAGCGCTGCCTCCAGGTTTTG
      R  L  D  F  L  R  D  H  V  R  F  F  Q  R  C  L  Q  V  L    36
 421 CCGGAGCGCTATTCTTCACTCGAGACAAGCAGGTTGACAATTGCATTTTTTGCACTCTCC
      P  E  R  Y  S  S  L  E  T  S  R  L  T  I  A  F  F  A  L  S  56
 481 GGGCTGGATATGTTGGATTCCTTAGATGTGGTGAACAAAGATGATATAATAGAGTGGATT
      G  L  D  M  L  D  S  L  D  V  V  N  K  D  D  I  I  E  W  I  76
 541 TATTCCCTGCAGGTCCTTCCCACAGAAGACAGATCAAATCTAAATCGCTGTGGTTTCCGA
      Y  S  L  Q  V  L  P  T  E  D  R  S  N  L  N  R  C  G  F  R  96
 601 GGCTCTTCATACCTGGGTATTCCGTTCAATCCATCAAAGGCTCCTGGAACAGCTCATCCT
      G  S  S  Y  L  G  I  P  F  N  P  S  K  A  P  G  T  A  H  P  116
 661 TATGATAGTGGCCACATTGCAATGACCTACACTGGCCTCTCATGCTTAGTTATTCTTGGA
      Y  D  S  G  H  I  A  M  T  Y  T  G  L  S  C  L  V  I  L  G  136
 721 GACGACTTAAGCCGAGTAAATAAAGAAGCTTGCTTAGCGGGCTTGAGAGCCCTTCAGCTG
      D  D  L  S  R  V  N  K  E  A  C  L  A  G  L  R  A  L  Q  L  156
 781 GAAGATGGGAGTTTTTGTGCAGTACCTGAAGGCAGTGAAAATGACATGCGATTTGTGTAC
      E  D  G  S  F  C  A  V  P  E  G  S  E  N  D  M  R  F  V  Y  176
 841 TGTGCTTCCTGTATTTGCTATATGCTCAACAACTGGTCAGGCATGGATATGAAAAAAGCC
      C  A  S  C  I  C  Y  M  L  N  N  W  S  G  M  D  M  K  K  A  196
 901 ATCACCTATATTAGAAGGAGTATGTCCTATGACAATGGACTGGCACAGGGAGCTGGACTT
      I  T  Y  I  R  R  S  M  S  Y  D  N  G  L  A  Q  G  A  G  L  216
 961 GAATCTCATGGAGGATCAACTTTTTGTGGCATTGCCTCACTATGTCTGATGGGTAAACTA
      E  S  H  G  G  S  T  F  C  G  I  A  S  L  C  L  M  G  K  L  236
1021 GAAGAAGTTTTTTCAGAAAAAGAATTGAACAGGATAAAGAGGTGGTGTATAATGAGGCAA
      E  E  V  F  S  E  K  E  L  N  R  I  K  R  W  C  I  M  R  Q  256
1081 CAAAATGGTTATCATGGAAGACCTAATAAGCCTGTAGACACCTGTTATTCTTTTTGGGTG
      Q  N  G  Y  H  G  R  P  N  K  P  V  D  T  C  Y  S  F  W  V  276
1141 GGAGCAACTCTGAAGCTTCTAAAAATTTTCCAATACACTAACTTTGAGAAAAATAGAAAT
      G  A  T  L  K  L  L  K  I  F  Q  Y  T  N  F  E  K  N  R  N  296
1201 TACATCTTATCAACTCAAGATCGCCTTGTAGGGGATTTGCCAAGTGGCCAGACAGTCAT
      Y  I  L  S  T  Q  D  R  L  V  G  G  F  A  K  W  P  D  S  H  316
1261 CCAGATGCTTTGCATGCATACTTTGGGATCTGTGGCCTGTCACTAATGGAGGAAAGTGGA
      P  D  A  L  H  A  Y  F  G  I  C  G  L  S  L  M  E  E  S  G  336
1321 ATTTGTAAAGTTCATCCTGCTCTGAATGTAAGCACACGGACTTCTGAACGCCTTCTAGAT
      I  C  K  V  H  P  A  L  N  V  S  T  R  T  S  E  R  L  L  D  356
1381 CTCCATCAAAGCTGGAAAACCAAGGACTCTAAACAATGCTCAGAGAATGTACATATCTCC
      L  H  Q  S  W  K  T  K  D  S  K  Q  C  S  E  N  V  H  I  S  376
1441 ACATGACTGATTTTAGATTGGGAGGGTGGGGGGGATTTGTAGCATAACTGTAGCTCAAGT
      T  *                                                          377
1501 TTAAAAGCCATGTATAACCAAGTGTGCTCTTTTTTTAAAAGGTAGAGTCTTACAATCAAA
1561 TCTCCTGCTGATTTCACTTTGGGATATGGTCTTGAGCCAGTAATCTTTATACTGGGTTTC
1621 AAGAAAATCTTTGTTGAAGTTTGAACCACAACTTTGTCGTGGTTCTTAAATGTTTATACT
1681 GTATTTCTAAGAAGTTGTTTGAGGCAAATTAACTGTATGTGTGTAGGTTATCTTTTTAAA
1741 AACTCTTCAGTGCAAATTGTATCTTATTATAAAATGGACACAAATTTTCAAGTTTACACT
1801 TCATATAGCATTGATAATCTTCAGGTGAACACTTAGTGATCATTTAAAAAGCTCACTGCT
1861 GATCGTAGAAAATTTGCTTTAATTAATTAAGTATCTGGGATTATTCTTTGAAAACAGATG
1921 ACCATAATTTTTTTTAAAGAAGAGTGACTTATTTTGTCTTATTCTTAAG 1969
```

Fig. 3

Insert sequence for pRD566 listed below:

```
GGATCCAGTA CTTATGGTAG CCACTGAGGA TGAGAGGCTA GCAGGGAGCGG
TGAGGGAGAG CGGCTGGATT TCTTACGGGA TCGGCACGTG CGATTTTTCC
AGCGCTGCCT CCAGGTTTTG CCGGAGCGCT ATTCTTCACT CGAGACAAGC
AGGTTGACAA TTGCATTTTT TGCACTCTCC GGGCTGGATA TGTTGGATTC
CTTAGATGTG GTGAACAAAG ATGATATAAT AGAGTGGATT TATTCCCTGC
AGGTCCTTCC CACAGAAGAC AGATCAAATC TAAATCGCTG TGGTTTCCGA
GGCTCTTCAT ACCTGGGTAT TCCGTTCAAT CCATCAAAGG CTCCTGGAAC
AGCTCATCCT TATGATAGTG GCCACATTGC AATGACCTAC ACTGGCCTCT
CATGCTTAGT TATTCTTGGA GACGACTTAA GCCGAGTAAA TAAAGAAGCT
TGCTTAGCGG GCTTGAGAGC CCTTCAGCTG GAAGATGGGA GTTTTTGTGC
AGTACCTGAA GGCAGTGAAA ATGACATGCG ATTTGTGTAC TGTGCTTCCT
GTATTTGCTA TATGCTCAAC AACTGGTCAG GCATGGATAT GAAAAAAGCC
ATCACCTATA TTAGAAGGAG TATGTCCTAT GACAATGGAC TGGCACAGGG
AGCTGGACTT GAATCTCATG GAGGATCAAC TTTTTGTGGC ATTGCCTCAC
TATGTCTGAT GGGTAAACTA GAAGAAGTTT TTTCAGAAAA AGAATTGAAC
AGGATAAAGA GGTGGTGTAT AATGAGGCAA CAAAATGGTT ATCATGGAAG
ACCTAATAAG CCTGTAGACA CCTGTTATTC TTTTTGGGTG GGAGCAACTC
TGAAGCTTCT AAAAATTTTC CAATACACTA ACTTTGAGAA AAATAGAAAT
TACATCTTAT CAACTCAAGA TCGCCTTGTA GGGGGATTTG CCAAGTGGCC
AGACAGTCAT CCAGATGCTT TGCATGCATA CTTTGGGATC TGTGGCCTGT
CACTAATGGA GGAAAGTGGA ATTTGTAAAG TTCATCCTGC TCTGAATGTA
AGCACACGGA CTTCTGAACG CCTTCTAGAT CTCCATCAAA GCTGGAAAAC
CAAGGACTCT AAACAATGCT CAGAGAATGT ACATATCTCC ACATGACTGA
TTTTAGATTG GGAGGGTGGG GGGGATTTGT AGCATAACTG TAGCTCAAGT
TTAAAAGCCA TGTATAACCA AGTGTGCTCT TTTTTTAAAA GGTAGAGTCT
TACAATCAAA TCTCCTGCTG ATTTCACTTT GGGATATGGT CTTGAGCCAG
TAATCTTTAT ACTGGGTTTC AAGAAATCT TTGTTGAAGT TTGAACCACA
ACTTTGTCGT GGTTCTTAAA TGTTTATACT GTATTCTAA GAAGTTGTTT
GAGGCAAATT AACTGTATGT GTGTAGGTTA TCTTTTTAAA AACTCTTCAG
TGCAAATTGT ATCTTATTAT AAAATGGACA CAAATTTTCA AGTTTACACT
TCATATAGCA TTGATAATCT TCAGGTGAAC ACTTAGTGAT CATTTAAAAA
GCTCACTGCT GATCGTAGAA AATTTGCTTT AATTAATTAA GTATCTGGGA
TTATTCTTTG AAAACAGATG ACCATAATTT TTTTTAAAGA AGAGTGACTT
ATTTTGTCTT ATTCTTAAG
```

Insert sequence for pRD577 listed below:

```
GGATCCATTGGAGGATGATTAAATGGCTGCTACTGAAGGTGTTGGTGAAGCTGCACAGGGT
GGTGAG CCCGGGCAG CCGGCGCAAC CCCCGCCCCA GCCGCACCCA
CCGCCGCCCC AGCAGCAGCA CAAGGAAGAG ATGGCGGCCG AGGCTGGGGA
AGCCGTGGCG TCCCCCATGG ACGACGGGTT TGTGAGCCTG GACTCGCCCT
CCTATGTCCT GTACAGGGAC AGAGCAGAAT GGGCTGATAT AGATCCGGTG
CCGCAGAATG ATGGCCCCAA TCCCGTGGTC CAGATCATTT ATAGTGACAA
ATTTAGAGAT GTTTATGATT ACTTCCGAGC TGTCCTGCAG CGTGATGAAA
GAAGTGAACG AGCTTTTAAG CTAACCCGGG ATGCTATTGA GTTAAATGCA
GCCAATTATA CAGTGTGGCA TTTCCGGAGA GTTCTTTTGA AGTCACTTCA
GAAGGATCTA CATGAGGAAA TGAACTACAT CACTGCAATA ATTGAGGAGC
AGCCCAAAAA CTATCAAGTT TGGCATCATA GGCGAGTATT AGTGGAATGG
CTAAGAGATC CATCTCAGGA GCTTGAATTT ATTGCTGATA TTCTTAATCA
GGATGCAAAG AATTATCATG CCTGGCAGCA TCGACAATGG GTTATTCAGG
AATTTAAACT TTGGGATAAT GAGCTGCAGT ATGTGGACCA ACTTCTGAAA
GAGGATGTGA GAAATAACTC TGTCTGGAAC CAAAGATACT TCGTTATTTC
TAACACCACT GGCTACAATG ATCGTGCTGT ATTGGAGAGA GAAGTCCAAT
ACACTCTGGA AATGATTAAA CTAGTACCAC ATAATGAAAG TGCATGGAAC
TATTTGAAAG GGATTTTGCA GGATCGTGGT CTTTCCAAAT ATCCTAATCT
GTTAAATCAA TTACTTGATT TACAACCAAG TCATAGTTCC CCCTACCTAA
TTGCCTTTCT TGTGGATATC TATGAAGACA TGCTAGAAAA TCAGTGTGAC
AATAAGGAAG ACATTCTTAA TAAAGCATTA GAGTTATGTG AAATCCTAGC
TAAAGAAAAG GACACTATAA GAAAGGAATA TTGGAGATAC ATTGGAAGAT
CCCTTCAAAG CAAACACAGC ACAGAAAATG ACTCACCAAC AAATGTACAG
CAATAAGAAT TAATTCGGTA CCCGGGATC CTCTAGAGTC GAGGAGTTTT
AAACTTATGG TAGCCACTGAGGAT GAGAGGCTAG CAGGGAGCGG
TGAGGGAGAG CGGCTGGATT TCTTACGGGA TCGGCACGTG CGATTTTTCC
AGCGCTGCCT CCAGGTTTTG CCGGAGCGCT ATTCTTCACT CGAGACAAGC
AGGTTGACAA TTGCATTTTT TGCACTCTCC GGGCTGGATA TGTTGGATTC
CTTAGATGTG GTGAACAAAG ATGATATAAT AGAGTGGATT TATTCCCTGC
AGGTCCTTCC CACAGAAGAC AGATCAAATC TAAATCGCTG TGGTTTCCGA
GGCTCTTCAT ACCTGGGTAT TCCGTTCAAT CCATCAAAGG CTCCTGGAAC
AGCTCATCCT TATGATAGTG CCACATTGC AATGACCTAC ACTGGCCTCT
CATGCTTAGT TATTCTTGGA GACGACTTAA GCCGAGTAAA TAAAGAAGCT
TGCTTAGCGG GCTTGAGAGC CCTTCAGCTG GAAGATGGGA GTTTTTGTGC
AGTACCTGAA GGCAGTGAAA ATGACATGCG ATTTGTGTAC TGTGCTTCCT
GTATTTGCTA TATGCTCAAC AACTGGTCAG GCATGGATAT GAAAAAAGCC
ATCACCTATA TTAGAAGGAG TATGTCCTAT GACAATGGAC TGGCACAGGG
AGCTGGACTT GAATCTCATG GAGGATCAAC TTTTTGTGGC ATTGCCTCAC
TATGTCTGAT GGGTAAACTA GAAGAAGTTT TTCAGAAAA AGAATTGAAC
AGGATAAAGA GGTGGTGTAT AATGAGGCAA CAAAATGGTT ATCATGGAAG
ACCTAATAAG CCTGTAGACA CCTGTTATTC TTTTTGGGTG GGAGCAACTC
TGAAGCTTCT AAAAATTTTC CAATACACTA ACTTTGAGAA AAATAGAAAT
TACATCTTAT CAACTCAAGA TCGCCTTGTA GGGGGATTTG CCAAGTGGCC
AGACAGTCAT CCAGATGCTT TGCATGCATA CTTTGGGATC TGTGGCCTGT
CACTAATGGA GGAAAGTGGA ATTTGTAAAG TTCATCCTGC TCTGAATGTA
AGCACACGGA CTTCTGAACG CCTTCTAGAT CTCCATCAAA GCTGGAAAAC
CAAGGACTCT AAACAATGCT CAGAGAATGT ACATATCTCC ACATGACTGA
TTTTAGATTG GGAGGGTGGG GGGATTTGT AGCATAACTG TAGCTCAAGT
TTAAAAGCCA TGTATAACCA AGTGTGCTCT TTTTTTAAAA GGTAGAGTCT
TACAATCAAA TCTCCTGCTG ATTTCACTTT GGGATATGGT CTTGAGCCAG
```

```
TAATCTTTAT ACTGGGTTTC AAGAAAATCT TTGTTGAAGT TTGAACCACA
ACTTTGTCGT GGTTCTTAAA TGTTTATACT GTATTTCTAA GAAGTTGTTT
GAGGCAAATT AACTGTATGT GTGTAGGTTA TCTTTTTAAA AACTCTTCAG
TGCAAATTGT ATCTTATTAT AAAATGGACA CAAATTTTCA AGTTTACACT
TCATATAGCA TTGATAATCT TCAGGTGAAC ACTTAGTGAT CATTTAAAAA
GCTCACTGCT GATCGTAGAA AATTTGCTTT AATTAATTAA GTATCTGGGA
TTATTCTTTG AAAACAGATG ACCATAATTT TTTTTAAAGA AGAGTGACTT
ATTTTGTCTT ATTCTTAAGG AATTCCTGCA GCCCGGGGGA TCCGTCGACC
TGCAGCCAAG CTT
```

PROTEIN PRENYLTRANSFERASE

This invention was made, at least in part, with support from the National Science Foundation (Grant No. DCB9105822) and the National Institutes of Health (Grant No. RO1 GM46372). The Government has certain rights in the invention.

TECHNICAL FIELD

The present invention relates, in general, to a protein prenyltransferase and, in particular, to protein geranylgeranyltransferase type I (GGTase-I) and to a nucleic acid sequence encoding same. The invention also relates to methods of producing GGTase-I and geranylgeranyl modified polypeptides. The invention further relates to methods of screening compounds for the ability to alter GGTase-I activity.

BACKGROUND

Covalent modification by isoprenoid lipids (prenylation) contributes to membrane interactions and biological activities of a rapidly expanding group of proteins (Maltese, FASEB J. 4:3319 (1990); Glomset et al, Trends Biochem. Sci. 15:139 (1990)). Either farnesyl (15-carbon) or geranylgeranyl (20-carbon) isoprenoids can be attached to specific proteins, with geranylgeranyl being the predominant isoprenoid found on proteins (Farnsworth et al, Science 247:320 (1990)). The prenyltransferase, protein geranylgeranyltransferase type-I (GGTase-I), transfers a geranylgeranyl group from the prenyl donor geranylgeranyl diphosphate to the cysteine residue of substrate proteins containing a C-terminal CAAX-motif in which "A" is any amino acid, including an aliphatic amino acid, and the "X" residue is leucine (Clarke, Ann. Rev. Biochem. 61:355 (1992); Casey, J. Lipid. Res. 330:1731 (1992)). Known targets of GGTase-I include γ-subunits of brain heterotrimeric G proteins and Ras-related small GTP-binding proteins such as Rac1, Rac2, Rap1A and Rap1B (Menard et al, Eur. J. Biochem. 206:537 (1992); Casey et al, Proc. Natl. Acad. Sci. USA 88:8631 (1991); Moores et al, J. Biol. Chem. 136:14603 (1991)). Additionally, short peptides encompassing the CAAX motif of these substrates can also be recognized by the enzyme (Casey et al, Proc. Natl. Acad. Sci. USA 88:8631 (1991); (Moores et al, J. Biol. Chem. 136:14603 (1991); Yokoyama et al, Proc. Natl. Acad. Sci. USA 88:5302 (1991)). Immobilization of one such peptide for use as an affinity matrix has led to the isolation of GGTase-I from bovine brain (Moomaw and Casey, J. Biol. Chem. 267:17438 (1992)). The purified enzyme contains two subunits with molecular masses of 48 kDa and 43 kDa, which have been designated, respectively, as α and β (henceforth designated $\beta_{GGI}$). GGTase-I is dependent on both $Mg^{2+}$ and $Zn^{2+}$ for optimal activity. Demonstration of the $Zn^{2+}$ dependence required prolonged incubation against, or purification in the presence of, a chelating agent. This property has led to the designation of GGTase-I as a zinc metalloenzyme (Moomaw and Casey, J. Biol. Chem. 267:17438 (1992)).

The properties of GGTase-I are similar to those of a related enzyme, protein farnesyltransferase (FTase). FTase transfers the prenyl moiety from farnesyl diphosphate to the cysteine residue of substrate proteins. FTase protein substrates, like those for GGTase-I, possess a C-terminal CAAX motif. The "X" residue of mammalian FTase substrates, however, is generally methionine, serine or glutamine as opposed to leucine for GGTase-I substrates (Moores et al, J. Biol. Chem. 136:14603 (1991); Moomaw and Casey, J. Biol. Chem. 267:17438 (1992)). Substrates for FTase include p21$^{ras}$ protein, lamin B and several proteins involved in visual signal transduction (Clarke, Ann. Rev. Biochem. 61:355 (1992)). Like GGTase-I, FTase is dependent upon $Mg^{2+}$ and $Zn^{2+}$ ions for optimal activity (Reiss et al, J. Biol. Chem. 267:6403 (1992)). Purified mammalian FTase is composed of two nonidentical subunits, α and β (henceforth designed βF), with apparent molecular masses of approximately 48 kDa and 46 kDa, respectively, on SDS-PAGE (Reiss et al, Cell 62:81 (1990)). cDNA clones encoding the FTase α and βF subunits have been isolated and their deduced amino acid sequences are homologous to the Saccharamoyces cerevisiae proteins Ram2 and Dpr1/Ram1, respectively, which encode the subunits of yeast FTase (Moores et al, J. Biol. Chem. 136:14603 (1991); Chen et al, Proc. Natl. Acad. Sci. USA 88:11368 (1991); Kohl et al, J. Biol. Chem. 266:18884 (1991); He et al, Proc. Natl. Acad. Sci. USA 88:11373 (1991)).

The 48 kDa α subunits of mammalian GGTase-I and FTase have been shown to be immunologically crossreactive, suggesting that these two enzymes share a common α subunit (Moomaw and Casey, J. Biol. Chem. 267:17438 (1992); Kohl et al, J. Biol. Chem. 266:18884 (1991); Seabra et al, Cell 65:429 (1991)). Similarly, a mutation in the S. cerevisiae gene RAM2, which encodes the α-like subunit of yeast FTase, results in a strain with defects in both GGTase-I activity and FTase activity (Moores et al, J. Biol. Chem. 136:14603 (1991); Kohl et al, J. Biol. Chem. 266:18884 (1991)). Further confirmation of a common subunit for yeast FTase and GGTase-I came from the bacterial coexpression of Ram2 with Ram1 that resulted in FTase activity (He et al, Proc. Natl. Acad. Sci. USA 88:11373 (1991)), while coexpression of Ram2 with Cdc43/Cal1 resulted in GGTase-I activity (Mayer et al, J. Biol. Chem. 267:20589 (1992)). Since the S. cerevisiae Cdc43/Cal1 subunit of GGTase-I shows amino acid similarity to yeast Ram1/Dpr1 and mammalian βF, it may be the yeast homolog of mammalian $\beta_{GGI}$ (Ohya et al, J. Biol. Chem. 266:12356 (1991)).

GGTase-I differs from the related enzyme Rab geranylgeranyltransferase, also called protein geranylgeranyltransferase type II (designated GGTase-II), which attaches a geranylgeranyl group to the COOH-terminal cysteines in small GTP-binding proteins that terminate in Cys-Cys or Cys-X-Cys motifs (Moores et al, J. Biol. Chem. 136:14603 (1991); Seabra et al, J. Biol. Chem. 267:14497 (1992); Horiuchi et al, J. Biol. Chem. 266:16981 (1991)). Target proteins of GGTase-II include Rab1A, which resides in the endoplasmic recticulum and Golgi complex, and Rab3A, a component of synaptic vesicles (Pfeffer, Trends. Cell. Biol. 2:41 (1992)). GGTase-II does not recognize COOH-terminal peptides corresponding to its target proteins, rather, substrate recognition appears to involve additional determinants on the Rab proteins (Moores et al, J. Biol. Chem. 136:14603 (1991); Khosravi-Far et al, J. Biol. Chem. 267:24363 (1992)). GGTase-II consists of three protein components. One component, the 95 kDa Rab escort protein, appears to bind substrate proteins and presents them to the catalytic subunits of the enzyme (Andres et al, Cell 73:1091 (1993)). The catalytic component of GGTase-II contains two tightly associated polypeptides with apparent molecular masses of 60 kDa and 38 kDa that, respectively, show similarity to the α and βF subunits of FTase (Armstrong et al, J. Biol. Chem. 268:12221 (1993)).

The present invention provides nucleic acid sequences encoding GGTase-I, in particular, the $\beta_{GGI}$ subunit. These sequences can be used to recombinantly produce GGTase-I.

The availability of large quantities of the enzyme permits the production of geranylgeranyl-modified proteins and peptides having diagnostic and therapeutic applications. In addition, the enzyme can be used to screen compounds for the potential to alter GGTase-I activity. Such compounds can be expected to be useful in pharmacological intervention strategies in areas including cancer and inflammation.

OBJECTS AND SUMMARY OF THE INVENTION

It is a general object of the invention to provide a nucleotide sequence encoding GGTase-I, particularly the β subunit thereof. It is a further object of the invention to provide a method of synthesizing GGTase-I, or the β subunit thereof, and a method of screening compounds for the ability to alter GGTase-I activity. Various other objects and advantages of the present invention will be apparent to those skilled in the art from a reading of the disclosure that follows.

In one embodiment, the present invention relates to an isolated nucleic acid encoding GGTase-I. In a further embodiment, the present invention relates to an isolated nucleic acid encoding the β subunit of mammalian GGTase-I, or portion thereof of at least 15 consecutive bases, or complement thereof. The invention also relates to recombinant molecules comprising such nucleic acids and vectors, and to host cells comprising same. In addition, the present invention relates to a method of producing GGTase-I or the β subunit of GGTase-I, or portion thereof, comprising culturing the above-described host cells under conditions such that the nucleic acid is expressed and GGTase-I or the β subunit of GGTase-I, or portion thereof, is thereby produced.

In a further embodiment, the present invention relates to an isolated nucleic acid consisting essentially of a double-stranded DNA molecule, one strand of which encodes the β subunit of mammalian GGTase-I, or portion thereof of at least 15 consecutive base pairs. The invention also relates to a recombinant molecule comprising such a nucleic acid operably linked to and in inverse orientation with respect to a promoter. The invention further relates to a method of inhibiting the production of GGTase-I in a host cell comprising introducing into the cell such a recombinant molecule under conditions such that the nucleic acid is transcribed and production of the GGTase-I is thereby inhibited.

In yet another embodiment, the present invention relates to a method of screening a test compound for the ability to alter GGTase-I activity. The method comprises comparing the GGTase-I activity of a sample in the presence and absence of the test compound, a reduction in the activity in the presence of the test compound being indicative of inhibitory activity of the test compound and an increase in the activity being indicative of an activating activity of the test compound.

BRIEF DESCRIPTION OF THE DRAWINGS

FIGS. 1 and 1A. Nucleotide (SEQ ID NO:1) and deduced amino acid (SED ID NO:2) sequences of rat GGTase-I $\beta_{GGI}$ subunit ($\beta_{GGI}$). Single letter abbreviations are used for the deduced amino acids.

FIG. 2. Nucleotide (SEQ ID NO:3) and deduced amino acid (SEQ ID NO:4) sequences of human GGTase-I $\beta_{GGI}$ subunit. The 3'-untranslated sequences and 5'-untranslated sequences are included. Single letter abbreviations are used for the deduced amino acids.

FIG. 3. Nucleotide sequence of intermediate pRD566 (SEQ ID NO:5), which contains the complete coding sequence for human $\beta_{GGI}$ and which is eventually translationally coupled to the coding sequence for human FPTase-α subunit.

FIGS. 4 and 4A. Nucleotide sequence of pRD577 (SEQ ID NO:6), which contains the complete coding sequence for human $\beta_{GGI}$ translationally coupled to the coding sequence for human FPTase-α subunit through a sequence which expresses the Glu-Glu-Phe epitope tag and contains the ribosomal binding site for expression of $\beta_{GGI}$.

DETAILED DESCRIPTION OF THE INVENTION

Figure 5:
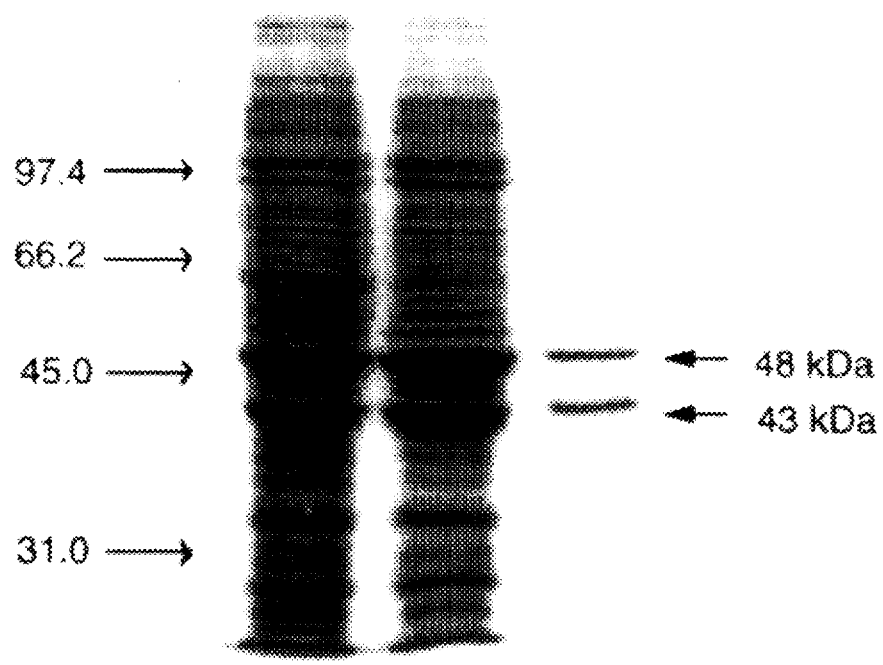
FIG. 5. SDS-PAGE analysis of GGTase-I obtained from Sf9 cell expression. Aliquots of pools obtained from each of the processing steps in the purification on an 11% acrylamide gel. Polypeptides were visualized by Coomassie Blue staining. The arrows indicate the migration positions of molecular weight standards; lane 1, 25 μg of the soluble extract; lane 2, 25 μg of the DEAE pool; lane 3, 1 μg of the Q-HP pool.

The present invention relates, in general, to a nucleic acid sequence encoding GGTase-I, particularly, the β subunit thereof, or portion of that encoding sequence. The invention further relates to the encoded protein, polypeptide or peptide. The term "portion", as used herein, and as applied to nucleic acid sequences, relates to fragments of at least 15 bases, preferably, at least 30 bases, more preferably, at least 150 bases and, most preferably, at least 300 bases. As applied to proteins, the term "portion" relates to peptides and polypeptides of at least 5 amino acids, preferably at least 10 amino acids, more preferably, at least 50 amino acids and most preferably, at least 100 amino acids. The invention also relates recombinant molecules comprising the above nucleic acid sequences and to host cells tranformed therewith. In addition, the invention relates to methods of making the protein, polypeptide or peptide encoded in the nucleic acid sequence by culturing the transformed host cells under appropriate conditions. Furthermore, the invention relates to methods of screening compounds for the ability to alter GGTase-I activity.

More specifically, the present invention relates to nucleotide sequences that encode the amino acid sequence of mammalian GGTase-I, particularly, the β subunit thereof, or portions thereof as defined above. In particular, the present invention relates to nucleotide sequences that encode the amino acid sequence given in SEQ ID NO:2 or SEQ ID NO:4 (see also FIGS. 1 and 2), or portions thereof as defined above (the DNA sequence given in SEQ ID NO:1 or SEQ ID NO:3, respectively, being only an example of each (see also FIG. 1 and FIG. 2)). Further, nucleotide sequences to which the invention relates include those encoding substantially the same protein as shown in SEQ ID NO:2 or SEQ ID NO:4, including, for example, intraspecies variations thereof, as well as functional equivalents of the sequences shown in SEQ ID NO:2 or SEQ ID NO:4. The invention further relates to nucleotide sequences substantially identical to the sequences shown in SEQ ID NO:1 and SEQ ID NO:3. A "substantially identical" sequence is one the complement of which hybridizes to the nucleic acid sequence of SEQ ID NO:1 or SEQ ID NO:3 at 42° C. in 4×saline/sodium citrate (SSC) containing 40% formamide and which remains bound when subjected to washing at 42° C. with 0.2×SSC containing 0.1% SDS (note: 20× SSC=3M sodium chloride/0.3M sodium citrate). The invention also relates to nucleic acids complementary to those described above.

The present invention also relates to a recombinant molecule comprising a nucleotide sequence as described above and to a host cell transformed therewith. Using standard methodologies, well known in the art, a recombinant molecule comprising a vector and a nucleotide sequence encoding GGTase-I (particularly, the β subunit thereof), or portion thereof as defined above, can be constructed. Vectors suitable for use in the present invention include plasmid and viral vectors. A plasmid vector into which a DNA sequence encoding the α and/or β subunits of a mammalian GGTase are cloned can be any vector compatible with transformation into a selected host cell, for example, a bacterial cell. Such vectors include, but are not limited to, derivatives of ColE1 (such as pBR322, pUC8, pUC9, pUC18, pUC19, and the like) (Yanish-Perron et al, Gene 33:103 (1985)) or P15a (such as pACYC177, pACYC184, and the like) (Chang and Cohen, J. Bacteriology 134:1141 (1978)). Other vectors suitable for use in the present invention include pGEM4Z, pVL1392 and pCMV. The nucleotide sequence of the invention can be present in the vector operably linked to regulatory elements, for example, a promoter. Suitable promoters include, but are not limited to, the tac promoter (Ammon et al, Gene 25:167 (1983)), lac promoter (Siebenlist et al, Cell 20:269 (1980)) and trp promoter (Bennet et al, J. Mol. Biol 121:113 (1978)). Such promoters use $E.\ coli$ RNA polymerase to transcribe DNA into mRNA. In one embodiment of the instant invention, the promoter is the tac promoter found in the plasmid pBTac1 (commercially available from Boehringer Mannheim Biochemicals). Other promoter/RNA polymerase systems suitable for use in the instant invention include RNA bacteriophage promoters and their cognate RNA polymerase. Examples of such systems include the bacteriophage T7 promoter and T7 RNA polymerase (Studier and Moffat, J. Mol. Biol. 189:113 (1986)). It is expected that the bacteriophage T7 promoter and RNA polymerase will give higher levels of protein expression than the tac promoter. Promoters derived from SP6, SV40, polyhedrin or adenovirus can also be used. When synthesis of GGTase-I is sought, sequences encoding the α and β subunits can be present in the same vector or in separate vectors. In either case, the sequences are, advantageously, transcribed independently.

As indicated above, the recombinant molecule of the invention can be constructed so as to be suitable for transforming a host cell. Suitable host cells include prokaryotic cells, such as bacteria, lower eukaryotic cells, such as yeast, and higher eucaryotic cells, such as mammalian cells, and insect cells. The recombinant molecule of the invention can be introduced into appropriate host cells by one skilled in the art using a variety of known methods.

The present invention further relates to a method of producing GGTase-I (particularly, the β subunit thereof), or portions thereof as defined above. The method comprises culturing the above-described transformed host cells under conditions such that the encoding sequence is expressed and the protein thereby produced.

The present invention further relates to GGTase-I (eg mammalian GGTase-I), particularly, the β subunit thereof, substantially free of proteins with which it is normally associated, or portions thereof as defined above. The proteins, polypeptides and peptides of the invention can be produced recombinantly using the nucleic acid sequences as described above, or chemically using known methods. The protein of the invention can be produced alone or as a fusion product, for example, with a protein such as glutathione S-transferase or maltose binding protein. Such fusion product can be produced recombinantly. For example, the coding sequence of the invention (eg the sequence encoding the β subunit of mammalian GGTase-I) can be cloned in frame with a sequence encoding another protein (such as glutatione-S-transferase or maltose binding protein) and the fusion product expressed in an appropriate host cell (see, for example, (Guan et al, Gene 67:21 (1987); Maina et al. Gene 74:365 (1988); Smith and Johnson, Gene 67:31 (1988)).

The proteins, polypeptides and peptides of the invention can be used as antigens to generate GGTase-I specific antibodies, particularly, antibodies specific for the β subunit of GGTase-I. Methods of antibody generation are well known in the art. Both monoclonal and polyclonal antibodies are contemplated, as are binding fragments thereof. One skilled in the art will appreciate that such antibodies can be used to selectively identify and isolate the proteins of the invention, eg. the β subunit of GGTase-I. Alternatively, the antibodies can be used in vivo or in vitro to block activity of the GGTase-I.

The present invention also relates to methods of using the proteins of the invention (eg, recombinantly produced GGTase-I) to screen compounds for their ability to alter (eg inhibit) GGTase-I activity, and thus to identify compounds that can serve, for example, as agonists or antagonists. In a typical screening assay, GGTase-I is incubated with geranylgeranyl diphosphate and a GGTase-I substrate (eg a protein or peptide that includes the CAAX motif recognized by GGTase-I) in the presence and absence of a compound the enzyme altering activity (eg the inhibitory potential) of which is to be tested. Incorporation of the geranylgeranyl group into the substrate is then determined. A reduction in enzyme activity (ie. a reduction in incorporation) in the test sample indicates that the test compound is an inhibitor of the enzyme. An increase in enzyme activity in the test sample indicates that the test compound is an activator of the enzyme. Such screening procedures are useful not only for identifying agents for their potential use in pharmacological intervention strategies in such areas as cancer and inflammation but also for distinguishing selectivity of inhibitors between GGTase-I and related enzymes such as FTase.

GGTase-I inhibitors include, but are not limited to, compounds having structures that mimic the specific substrates of GGTase-I. Thus, analogs of geranylgeranyl diphosphate might be expected to show specificity of interaction toward GGTase-I but not FTase (Moomaw and Casey, J. Biol. Chem. 267:17438 (1992); Moores et al, J. Biol. Chem. 266:14603 (1991)). Similarly, CAAX-containing peptides in which the C-terminal residue is leucine also interact strongly with GGTase-I but poorly with FTase and such peptides or their analogs (eg peptidomimetics (see, for example, Kohl et al, Science 260:1934 (1993)) can be used as specific inhibitors of GGTase-I (Casey et al, Proc. Natl. Acad. Sci. USA 88:8631 (1991); Yokoyama et al, Proc. Natl. Acad. Sci. USA 88:5302 (1991)). Other potential inhibitors of GGTase-I include chemical compounds (eg chelators) that specifically interact with the zinc atom contained in GGTase-I that is required for enzymatic activity (Moomaw and Casey, J. Biol. Chem. 267:17438 (1992)).

The nucleic acid and amino acid sequences of the invention have diagnostic and therapeutic applications. For example, peptides representing portions of $\beta_{GGI}$ that specifically bind to substrate proteins and block their modification (eg peptides that mimic the active site environment of GGTase-I subunits) by preventing recognition by GGTase-I. GGTase-I activity can also be blocked by reducing or eliminating the expression of $\beta_{GGI}$ For example, antisense oligonucleotides complementary to $\beta_{GGI}$ mRNA can be used to selectively diminish or oblate the expression of the protein (see, for example, Calabrietta, Cancer Research 51:4505 (1991)). In addition, catalytic RNA molecules ("ribozymes") can be used to selectively cleave the $\beta_{GGI}$ mRNA and thereby prevent its translation (see, for example, Sullenger and Cech, Science 262:1566 (1963)). Inhibition of GGTase-I activity is advantageous in clinical settings in which GGTase-I is abberantly activated (see Ando et al, J. Biol. Chem. 267:25709 (1992) and Heyworth et al, J. Mol. Biol. Cell 4:261 (1993) for discussion of effect of GGTase-I on protein activation).

The present invention also relates to pharmaceutical compositions comprising the proteins, peptides, or nucleic acids of the invention. The invention also relates to compositions comprising compounds selected using the above-described screening protocol. Such compositions include the active agent in combination with a pharmaceutically acceptable carrier. The amount of active agent in the composition can vary with the agent, the patient and the effect sought. Likewise, the dosage regimen will vary depending on the composition and the disease/disorder to be treated.

Certain aspects of the invention are described in greater detail in the non-limiting Examples that follow.

EXAMPLES

Methodologies and reagents used in at least certain of the Examples below are as follows:

Molecular biology techniques used include those described by Sambrook et al (Molecular Cloning: A Laboratory Manual, Cold Spring Harbor Laboratory Press, Cold Spring Harbor, N.Y. (1990)) and Saiki et al (Science 239:487 (1988)). Enzymes were obtained from New England Biolabs (Beverly, Mass.) or Boehringer-Mannheim (Indianapolis, Ind.). cDNA clones were subcloned into pGEM-4Z or pUC18 or pUC19 and sequenced by the dideoxy chain termination method (Sanger et al, Proc. Natl. Acad. Sci. USA 74:5463 (1977)) using universal primers or specific internal primers. All cDNAs and PCR products were sequenced on both strands. [$^{32}$P]-labelled DNA probes were synthesized using a random primer labeling kit (BRL or Boehringer-Mannheim) and [$^{32}$P]dNTPs (Amersham). Total cellular RNA was isolated from tissue by the guanidinium thiocyanate/CsCl centrifugation procedure (Chirgwin et al. Biochem. 18:5294 (1979)). Poly(A)$^+$ RNA was isolated by oligo(dT)-cellulose chromatography (Sambrook et al. Molecular Cloning: A Laboratory Manual, Cold Spring Harbor Laboratory Press, Cold Spring Harbor, N.Y. (1990)).

Example I

Protein Sequence Determination of GGTase-I

Approximately 1 nmol of GGTase-I purified from bovine brain using affinity chromatography as described (Moomaw and Casey, J. Biol. Chem. 267:17438 (1992)) was subjected to electrophoresis on a 11% SDS-polyacrylamide gel and transferred to nitrocellulose paper. The nitrocellulose paper was then stained with Ponceau S to localize the subunit polypeptides. The 48 kDa and 43 kDa bands (corresponding to the $\alpha$ and $\beta_{GGI}$ polypeptide components, respectively) were excised from the nitrocellulose and sent to Harvard Microchem (Cambridge, Mass.) for processing. Briefly, this involved digestion in situ with trypsin, isolation of peptides produced by microbore HPLC, and sequence determination (Aebersold et al, Proc. Natl. Acad. Sci. USA 84:6970 (1987)).

High-confidence sequences of three $\alpha$ subunit peptides and five $\beta_{GGI}$ subunit peptides clearly resolved by HPLC were obtained. A sequence comparison between the peptides obtained from the 48 kDa $\alpha$ subunit of bovine GGTase-I and corresponding regions of bovine FTase-$\alpha$ as deduced from a cDNA clone (Kohl et al, J. Biol. Chem. 266:18884 (1991)) are shown (Table I).

TABLE I

Amino Acid sequence of GGTase-I $\alpha$ and $\beta_{GGI}$ peptides

| $\alpha$ Peptide | Corresponding peptide from Bovine FTase $\alpha$ |
|---|---|
| 1 FQDVYDYFR (SEQ ID NO:7) | FQDVYDYFR (aa 46–54) |
| 2 QWVIQEFK (SEQ ID NO:8) | QWVIQEFK (aa 157–164) |
| 3 VLVEWLRDPSQELEFIADILTQDAK (SEQ ID NO:9) | VLVEWLRDPSQELEFIADILTQDAK (aa 124–148) |

| $\beta_{GGI}$ peptide | Location of peptide (aa) in mammalian $\beta_{BGGI}$ open reading frames |
|---|---|
| 1 TIAFFALSGLDMLD (SEQ ID NO:10) | 49–62 |
| 2 GSSYLGIPFNPSK (SEQ ID NO:11) | 97–109 |
| 3 IFQYTNFEK (SEQ ID NO:12) | 285–293 |
| 4 NYILSTQDR (SEQ ID NO:13) | 296–304 |
| 5 DLHQSWK (SEQ ID NO:14) | 356–362 |

The purified 48 kDa $\alpha$ subunit and 43kDa $\beta_{GGI}$ subunits of bovine brain GGTase-I were digested with trypsin and the resulting peptides were purified by HPLC and sequenced. The GGTase-I $\alpha$ subunit peptides are shown compared to peptides deduced from a cDNA encoding the bovine FTase $\alpha$ subunit (Kohl et al, J. Biol. Chem. 266:18884–18888 (1991)).

Three different peptides from the $\alpha$ subunit of GGTase-I were sequenced and found to be 100% identical to regions of FTase $\alpha$ indicating that both GGTase-I and FTase share a common subunit (see also Example III below).

Example II

Cloning of the Mammalian GGTase-I $\beta_{GGI}$ Subunit cDNA

Two degenerate oligonucleotide primers |GCTC-GGATCC-C-(A/G)AA-(A/G)TT-NGT-(A/G)TA-(T/C)TG-(A/G)A (SEQ ID NO:15) and GTCG-GAATTC-ACN-AT(A/C/T)-GCN-TT(C/T)-TT(C/T)-GC (SEQ ID NO:16)| were synthesized based on portions of two $\beta_{GGI}$ subunit peptide sequences |IFQYTNFEK (SEQ ID NO:12) (antisense oligo) and TIAFFLSGLDMLD (SEQ ID NO:10) respectively|. The polymerase chain reaction (PCR) (Saiki et al. Science 239:487 (1988)) was performed using DNA obtained from a bovine brain cDNA library as template (Vogel et al. Nature 335:90 (1988)). A 730 bp PCR product was isolated (SEQ ID NO:26) that hybridized to a degenerate oligonucleotide |GTAC-TCTAGA-GGN-AT(A/C/T)-CCN-TT(T/C)-AA(T/C)-CC (SEQ ID NO:17)| encoding part of the peptide GSSYLGIPFNPSK (SEQ ID NO:11) (peptide 2 in Table I). The PCR fragment was cleaved with EcoRI and BamHI (restriction sites in the PCR oligos) and cloned into pUC19 creating pRD548.

To isolate human cDNAs encoding the $\beta_{GGI}$ subunit, a 300 bp EcoRI-HindIII fragment containing the N-terminal portion of the coding sequence in pRD548 was [$^{32}$P]-labelled and used to screen approximately $10^6$ plaques each from both a human placenta cDNA library in $\lambda$gt11 (Clonetech) and a human kidney cDNA library in $\lambda$max1 (Clonetech) as described (Kohl et al. J. Biol. Chem. 266:18884 (1991)). Six cDNA clones were isolated from the human placenta cDNA library and seven were isolated from the human kidney cDNA library. Phage from the $\lambda$gt11 library were isolated and the cDNA inserts subcloned into pUC18 as EcoRI fragments. cDNA inserts from clones from the $\lambda$max1 library were exised as phagemids. A plasmid containing the 1.55 kb cDNA from clone 3 from the human placenta cDNA library was designated pRD550. The insert in pRD550 contains all but the N-terminal 36 codons for $\beta_{GGI}$. The phagemid containing the 0.7 kb cDNA from clone 27 from the human kidney cDNA library was designated pRD558. The insert in pRD558 encodes the N-terminal 123 amino acids of $\beta_{GGI}$. Construction of a plasmid with the complete human $\beta_{GGI}$ coding sequence was caried out as follows: PCR was performed on pRD558 placing a BamHI and ScaI site upstream of the $\beta_{GGI}$ start codon. This DNA was cleaved with BamHI and XhoI, which cleaves within the $\beta_{GGI}$ coding sequence, creating fragment 1 of 0.13 kb. Fragment 2 was a 1.52 kb XhoI-EcoRI fragment from pRD550 that contained the coding sequence downstream of the XhoI site. Fragments 1 and 2 were cloned into BamHI-EcoRI digested pUC18 creating pRD566 which contains the complete coding sequence for human $\beta_{GGI}$ and 3'-untranslated sequences. The base sequence for pRD566 is shown in FIG. 3.

To isolate rat cDNAs encoding the $\beta_{GGI}$ subunit, the PCR probe from pRD548 was labeled and used to screen a rat brain 5'-stretch cDNA $\lambda$gt10 library (Clontech). Duplicate filters were hybridized in 4×SSC (1×SCC=150 mM NaCl/15 mM sodium citrate, pH=7) and 40% formamide (Sambrook et al. Molecular Cloning: A Laboratory Manual, Cold Spring Harbor Laboratory Press, Cold Spring Harbor, N.Y. (1990)) at 42° C. with 2×10$^6$ cpm of [$^{32}$P]-labeled probe per ml of hybridization buffer. The filters were washed in 2×SSC, 0.1% SDS twice for 15 min at 42° C. and then in 0.2×SCC, 0.1% SDS for 30 min at 42° C. Of the 1×10$^6$ plaques that were screened, five positives were identified and plaque purified. The clone with the longest 5'-end (designated as clone 22) was subcloned into pGEM-4Z and sequenced on both strands. DNA sequencing of the clone indicated that it contains all but the first two codons of the rat $\beta_{GGI}$ subunit.

To isolate the N-terminal coding sequence for rat $\beta_{GGI}$, the 5'-rapid amplification of cDNA ends (RACE) procedure was used to extend the 5'-end of clone 22 (Frohman in PCR Protocols: A Guide to Methods and Applications (Innis et al. eds.), pp. 28–38, Academic Press, San Diego (1990)). Three primers were prepared based on the 5'-end sequences of clone 22. First strand cDNA was synthesized from rat brain mRNA with one of the primers and the cDNA was then tailed with dATP using terminal transferase. Two rounds of PCR reactions were performed using the two nested primers and an oligo dT primer. The RACE products obtained were cloned into pGEM-4Z. Twelve clones from different PCR reactions were sequenced on both strands and all yielded identical sequences. The DNA sequence of these clones contained an in frame ATG codon 3 base pairs upstream of the 5'-end of the cDNA in clone 22. This ATG codon is in the same position as the initiation codon found in the cDNA sequence of human $\beta_{GGI}$ (FIG. 2).

A cDNA encoding the complete rat $\beta_{GGI}$ subunit of GGTase-I was obtained by a combination of screening with the 730 bp PCR probe and RACE techniques as described above. The nucleotide sequence of the cDNA encoding the $\beta_{GGI}$ subunit of rat GGTase-I is shown in SEQ ID NO:1. The cDNA sequence contains an ATG initiation codon and encodes a protein of 377 amino acids that contains all five peptides the sequences of which were obtained from tryptic digestion of the purified $\beta_{GGI}$ subunit (see Table I of Example I). The predicted molecular mass of the cloned rat $\beta_{GGI}$ polypeptide, 42.4 kDa, is very similar to the 43 kDa observed on SDS-PAGE for the $\beta_{GGI}$ subunit of the enzyme purified from bovine brain (Moomaw and Casey, J. Biol. Chem. 136:14603 (1991)).

An alignment of the amino acid sequences of the rat and human GGTase-I $\beta_{GGI}$ subunits, together with other protein prenyltransferase β subunits, was made. These additional β subunits included those for rat FTase (Chen et al. Cell 66:327 (1991)), rat GGTase-II (Armstrong et al. J. Biol. Chem. 268:12221 (1993)) and the CDC43 gene product of S. cerevisiae (Ohya et al. J. Biol. Chem. 266:12356 (1991)). Only 10 of 377 amino acids differ between rat and human GGTase-I $\beta_{GGI}$ subunits, and seven of the ten substitutions involve conservative amino acid changes. In general, the C-terminal regions are more conserved among the protein prenyltransferase β subunits than are the N-terminal regions. Exceptions are the N-terminal regions of the $\beta_{GGI}$ subunits of rat and human GGTase-I and Cdc43, which show higher homology to one another than to other protein prenyltransferase β subunits. This observation is consistent with the proteins being β subunits of GGTase-I from different species.

Example III

Expression and Purification of Recombinant GGTase-I and FTase a) Expression of human GGTase-I in *E. coli:*

To express human GGTase-I in *E. coli*, the cloned human $\beta_{GGI}$ subunit cDNA and the previously cloned human FTase-α subunit cDNA (Omer et al. Biochem. 32:5167 1993)) were coexpressed in a translationally coupled plasmid. In *E. coli*, the plasmid pT5T-hFPTase-α expresses the human a subunit protein with a C-terminal Glu-Glu-Phe epitope tag from a bacteriophage T7 promoter. The plasmid pT5T-hFPTase-α was obtained as described by Omer et al. (Biochem. 32:5167 (1993)). Specifically, the coding region of the α subunit of human FPTase was modified by PCR (Saiki et al. Science 239:487 (1988)) such that EcoRI restriction sites were placed immediately upsteam and

```
BamHI
G-GAT-CCA-TTG-GAG-GAT-GAT-TAA ATG GCT GCT ACT GAA GGT GTT GGT GAA GCT GCA CAG GGT GGT
   D   P   L   E   D   D   stop  M   A   A   T   E   G   V   G   E   A   A   Q   G   G
GAG CCC-α codons aa₁₇-aa₃₇₉-GAG GAG TTT TAA TTAA GAATTC- PstI-SmaI-BamHI-SalI-PstI-HindIII (SEQ ID NO:21
 E   P                       E   E   F   stop PacI EcoRI
and SEQ ID NO:22 SEQ ID NO:27)
``` downstream of the α subunit coding sequence and cloned into pUC18 to create pRD452. The sequence of the insert of pRD452 is as follows:

```
GAATTC-ATGα codons for aa₂-aa₃₇₉-TAA-GAATTC-
EcoRI    M                        Stop EcoRI
(SacI-KpnI-SmaI-BamHI-HincII-PstI-SphI-HindIII) pUC18 polylinker
``` pRD452 was cut with SacI, which only cuts in the polylinker region of the plasmid, the ends blunted with T4 DNA polymerase and dNTPs and then recircularized. This plasmid was partially digested with EcoRI, the ends filled in with the Klenow fragment of E. coli DNA polymerase and dNTPs and recircularized. A plasmid from this step, in which the EcoRI site downstream of the coding sequence for the α subunit of human FPTase was filled in, was identified and named pRD494. The sequence of the insert in pRD494 is the following:

```
GAATTC-ATGα subunit codons aa₂-aa₃₇₉-TAA-GAATTAATTC-
EcoRI    M                              stop
(KpnI-SmaI-BamHI-HincII-Psti-SphI-HindIII) (SEQ ID NO:18).
```

The SacI restriction endonuclease site in this plasmid was completely lost. Synthetic oligonucleotides encoding an approximately 70 bp EcoRI-BanII fragment at the 5'-end of the α subunit coding sequence were made that contained primarily A or T at the third position of each codon, and inserted into pRD494 that had been cut with EcoRI and BanII to create pRD493. The sequence of the α subunit coding sequence and the surrounding restriction sites in pRD493 are as follows:

The coding sequence for the human β_{GGI} protein was cloned downstream of the α subunit coding sequence in pT5T-hFPTase-α as follows. Fragment 1, a 0.5 kb SpeI-XhoI fragment, containing the sequence CT between the C-terminus of α and the N-terminus of the β_{GGI} subunit coding sequences was made by recombinant PCR using pT5T-hFPTase-α and pRD566 as templates (Higuchi(1990) in PCR Protocols: A Guide to Methods and Applications (Innis, M. A., Gelfand, D. H., Sninsky, J. J. & White, T. J., eds.), pp. 177–183, Academic Press, San Diego). Fragment 2, a 1.52 kb XhoI-EcoRI fragment from pRD566 contained the part of the β_{GGI} coding sequence not in fragment 1. Fragment 3 was a 6.2 kb SpeI (partial digestion)-EcoRI fragment from pT5T-hFPTase-α that contained the portion of the α coding sequence not in fragment 1 and the vector and promoter sequences from pT5T-hFPTase-α. Fragments 1, 2 and 3 were ligated together to create pRD577 which has the following structure:

```
GAATTCTAGATAT-  ATG GCT GCT ACT GAA GGT GTT GGT GAA GCT GCA CAG GGT GGT-
EcoRI           M   A   A   T   E   G   V   G   E   A   A   Q   G   G
codons for aa₁₅-aa379 of α subunit of FPTase-TAA-GAATTAATTC-
                                                 stop
(KpnI-SmaI-BamHI-HincII-PstI-SphI-HindIII) (SEQ ID NO:19 and SEQ ID NO:20)
```

The 5'-end of the α subunit coding region of pRD493 was modified by PCR placing a BamHI site along with additional sequences that would facilitate translational coupling of the α subunit to the φ10 coat protein. This 0.8 kb BamHI-SpeI fragment was ligated with a SpeI-HindIII fragment from pRD471 to BamHI-HindIII cut pT5T (Eisenberg et al. Nature 343:341 (1990)) creating pT5T-FPTaseα. The sequence of the insert in pT5T-FPTase-α is as follows:

| RBS | | |
|---|---|---|
| pT5T - α coding -GAG-GAG-TTT-TAA-CTT-ATG-GTA- $\beta_{GGI}$ coding (SEQ ID NO:23) | | |
| E E F stop | | |

The coding sequence for the human $\beta_{GGI}$ subunit was translationally coupled to the α subunit coding sequence with the ribosomal binding site (RBS), for expression of $\beta_{GGI}$, within the Glu-Glu-Phe epitope tag. The base sequence for pRD577 is shown in FIG. 3.

To express human GGTase-I, pRD577 was transformed into E. coli BL21(DE3), creating strain RD578 (deposited at the American Type Culture Collection, 12301 Parklawn Drive, Rockville, Md., on Jan. 28, 1994, and was given accession number 69545, grown and induced with 0.5 mM isopropyl-β-D-thiogalactoside as described (Omer et al. Biochemistry 32:5167 (1993)). Recombinant, human GGTase-I was purified from the cells essentially as described for human FTase using a YL1/2 antibody column, which binds the Glu-Glu-Phe epitope tag on the α subunit, and an optional MonoQ HR 5/5 column (Omer et al. Biochemistry 32:5167 (1993)). The GGTase-I eluted from the MonoQ column at approximately 0.25M NaCl.

b) Expression of rat GGTase-I in Sf9 cells:

The rat $\beta_{GGI}$ cDNA was subcloned using standard procedures into PVL1392 vector, the resulting plasmid is termed PVL1392-$\beta_{GGI}$. The entire coding region of the FTase-α subunit cDNA (obtained from ATCC) was also subcloned into PVL1392 (PVL1392-α). To generate recombinant baculoviruses, Sf9 cells were transfected with 0.5 µg of wild-type viral DNA (PharMingen) and 2 µg of both PVL11392-$\beta_{GGI}$ and PVL1392-α. The recombinant viruses obtained were purified by standard procedures (Summers and Smith, Texas Agricultural Experiment Station, Bulletin #1555 (1987)) and used to infect one liter of Sf9 cells at a multiplicity of infection of 5. Cells were harvested at 75 hr post-infection and an extract prepared. GGTase-I was purified from the soluble fraction of the extract by sequential chromatography on DEAE-Sephacel and Q-HP resins. SDS-PAGE analysis of purified GGTase-I showed the expected composition of subunit polypeptides at ~48 kDa and ~43 kDa (FIG. 5).

Anti-peptide antisera were produced to both $\beta_{GGI}$ and FT-α. For $\beta_{GGI}$, the synthetic peptide containing the sequence [C]GSSYLGIPFNPSK (SEQ ID NO:24) representing the deduced amino acid sequence from aa97 to aa109 in the $\beta_{GGI}$ cDNA with an appended Cys residue for crosslinking to keyhole limpet hemocyanin (KLH). For FT-α, the synthetic peptide was IGRSLQSKHSTE[C] (SEQ ID NO:25) representing the deduced amino acid sequence from aa359 to aa371 in the rat FT-α cDNA (Chen et al. Proc. Natl. Acad. Sci. USA 88:11368 (1991)) with an appended Cys residue. Both peptides were coupled to KLH through the cysteine residues and sent to Noble Research, Inc. for immunization of rabbits and sera production. Immunoblotting using the immune sera was performed as previously described (Mumby and Gilman, Meth. Enzymol. 195:215 (1989)). The antisera raised to the $\beta_{GGI}$ peptide specifically recognized the 43 kDa polypeptide in purified recombinant GGTase-I while the antisera raised to the FT-α peptide specifically recognized the 48 kDa polypeptide.

Example IV

Enzymatic Properties of Recombinant GGTase-I

Enzyme activity of human GGTase-I prepared using the YLY2 antibody column was compared to that for human FTase in the use of protein substrates Ras-CVLS or Ras-CAIL and lipid substrates farnesyl diphosphate (FPP) and geranylgeranyl diphosphate (GGPP) (Moores et al. J. Biol. Chem. 136:14603 (1991); Yokoyama et al Proc. Natl. Acad. Sci. USA 88:5302 (1991), Moomow et al J. Biol. Chem. 267:17438 (1992)).

Enzymatic activity of recombinantn human GGTase-I

| | $nmol \cdot h^{-1} \cdot mg^{-1}$ | |
|---|---|---|
| Substrates | FTase | GGTase-I |
| Ras-CVLS + FPP | 840 | <1 |
| Ras-CAIL + FPP | 66 | 6.6 |
| Ras-CVLS + GGPP | 19 | <1 |
| Ras-CAIL + GGPP | <1 | 1060 |

Purified recombinant human GGTase-I and FTase were assayed for activity using the substrates a) Ras-CVLS (1 mM) and [$^3$H] FPP (0.5 mM) [Ras-CVLS+FPP], b) Ras-CAIL (1 mM) and [$^3$H] FPP (0.5 mM) [Ras-CAIL+FPP], c) Ras-CVLS (1 mM) and [$^3$H] GGPP (0.5 mM) [Ras-CVLS+GGPP] and d) Ras-CAIL (1mM) and [$^3$H] GGPP [Ras-CAIL+GGPP] as described (Moores et al. J. Biol. Chem. 136:14603 (1991)). Briefly, 100 ng of GGTase-I or FTase was incubated in a 300 ml reaction at 30° C. and 50 ml aliquots removed after 2, 4, 6, 8 and 10 min and acid/ethanol insoluble radioactivity determined. Each assay was performed in duplicate and the rates of incorporation (nmol h$^{-1}$ mg$^{-1}$) were determined and the mean value of the duplicates is shown.

The data indicate that the E. coli expressed human GGTase-I enzyme preferentially uses Ras-CAIL and GGPP as substrates in contrast to FTase which preferentially uses Ras-CVLS and FPP as substrates. This is as seen for these two enzymes when isolated from a natural source such as bovine brain (Moores et al. J. Biol Chem. 136:14603 1991, Moomaw and Casey, J. Biol. Chem. 267:17438 (1992)). The specific activity of the E. coli expressed GGTase-I is similar to the value for GGTase-I purified from bovine brain (490 nmol h$^{-1}$ mg$^{-1}$, Moomaw and Casey, J. Biol. Chem. 267:17438 (1992)). Thus the recombinant, human GGTase-I appears to be similar to enzyme from a natural source.

Figure 6:
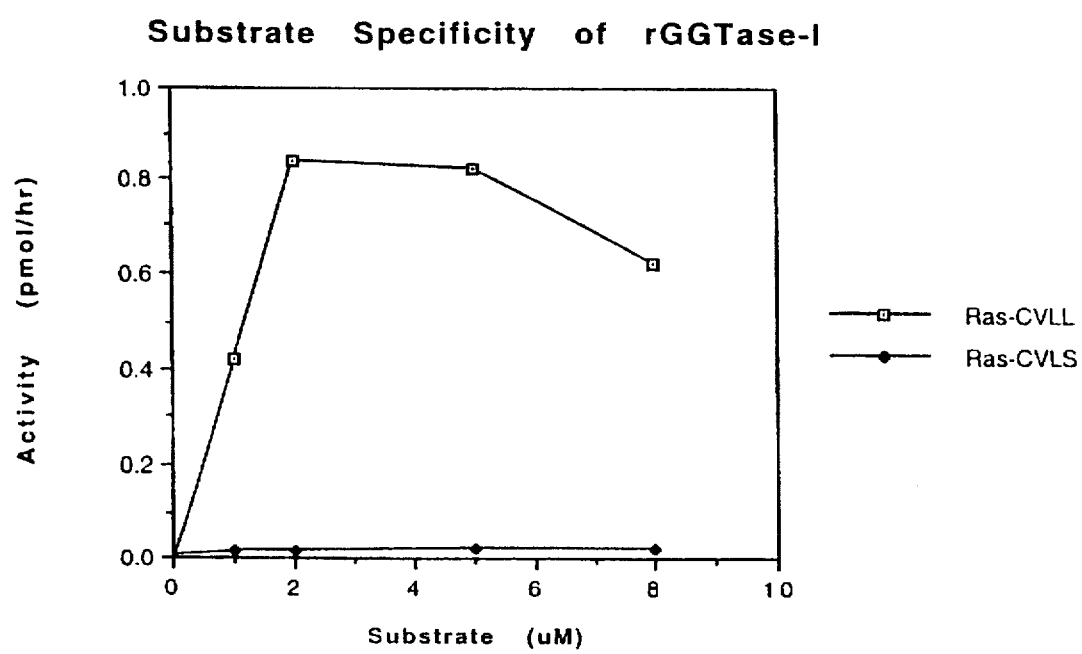
FIG. 6. Protein substrate specificity of purified recombinant GGTase-I. Assays were conducted by standard procedures (Casey et al, Proc. Natl. Acad. Sci. USA 88:8631 (1991); Moomaw and Casey, J. Biol. Chem. 267:17438 (1992)) and each reaction mixture contained the indicated concentration of substrate protein. Symbols used are (□), ras-CVLL; (♦), ras-CVLS.

Purified recombinant rat GGTase-I was assayed to determine whether its enzymatic properties were similar to GGTase-I isolated from a natural source. The results of one such experiment are shown (FIG. 6). The assay conditions and the production of substrate proteins were described (Casey et al. Proc. Natl. Acad. Sci. USA 88:8631 (1991); Moomaw and Casey, J. Biol. Chem. 267:17438 (1992)). Recombinant GGTase-I can efficiently modify a ras protein containing a leucine residue at the C-terminus (Ras-CVLL), but not one containing a serine residue (Ras-CVLS). Ras-CVLS is instead a good substrate for FTase (Casey et al. Proc. Natl. Acad. Sci. USA 88:8631 (1991); Reiss et al. Cell 62:81 (1990)). Additionally, recombinant GGTase-I can specifically recognize short CAAX-type peptides containing a leucine residue at the C-terminus in a fashion indistinguishable from that of the enzyme purified from mammalian tissue (Casey et al, Proc. Natl. Acad. Sci. USA 88:8631 (1991)).

All documents cited above are hereby incorporated in their entirety by reference.

One skilled in the art will appreciate from a reading of this disclosure that various changes in form and detail can be made without departing from the true scope of the invention.

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
( A ) LENGTH: 1568 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| GGACAGCGCA | TGGCGGCCAC | AGAGGATGAC | AGACTGGCGG | GGAGCGGAGA | AGGAGAACGG | 60 |
| CTGGATTTCC | TGCGGGACCG | ACACGTGCGG | TTCTTCCAGC | GCTGCCTCCA | GGTCTTGCCG | 120 |
| GAGCGGTATT | CTTCGCTGGA | GACCAGCAGG | CTGACAATTG | CATTTTTTGC | ACTCTCTGGG | 180 |
| CTGGATATGT | TGGACTCCTT | GGATGTGGTG | AACAAAGACG | ATATAATAGA | GTGGATTTAT | 240 |
| TCCTTGCAGG | TTCTTCCCAC | AGAAGACAGG | TCAAATCTGG | ATCGCTGTGG | TTTCCGAGGT | 300 |
| TCTTCATATT | TGGGTATTCC | ATTCAACCCA | TCAAAGAATC | CAGGCACAGC | TCATCCTTAT | 360 |
| GACAGTGGAC | ACATAGCGAT | GACTTACACT | GGTCTTTCCT | GTTAATTAT | TCTTGGAGAT | 420 |
| GATTTAAGCC | GAGTAGATAA | AGAAGCTTGC | TTAGCAGGCT | TGAGAGCACT | TCAGCTGGAA | 480 |
| GATGGGAGCT | TCTGTGCTGT | TCCTGAAGGC | AGTGAGAATG | ACATGAGGTT | TGTGTACTGT | 540 |
| GCTTCCTGCA | TTTGCTATAT | GCTCAACAAC | TGGTCAGGCA | TGGATATGAA | GAAAGCCATC | 600 |
| AGCTACATTA | GAAGAAGTAT | GTCCTATGAC | AATGGCCTGG | CACAGGGGGC | AGGACTTGAG | 660 |
| TCTCATGGAG | GATCCACCTT | TTGTGGCATT | GCGTCACTGT | GCCTGATGGG | TAAACTGGAA | 720 |
| GAAGTTTTTT | CAGAGAAAGA | ACTGAACCGG | ATAAAGAGGT | GGTGCATAAT | GAGGCAGCAG | 780 |
| AACGGGTACC | ACGGAAGACC | TAACAAGCCT | GTCGACACCT | GTTACTCTTT | CTGGGTGGGA | 840 |
| GCAACACTAA | AGCTTTTGAA | AATTTTCCAG | TACACTAACT | TTGAGAAGAA | TAGGAATTAC | 900 |
| ATCTTATCAA | CTCAGGATCG | CCTTGTTGGG | GGATTTGCTA | AATGGCCAGA | CAGTCATCCA | 960 |
| GATGCTTTGC | ATGCGTACTT | CGGGATCTGT | GGCCTGTCAC | TAATGGAGGA | GAGTGGAATT | 1020 |
| TGTAAAGTTC | ATCCTGCTCT | GAATGTAAGC | ACACGAACTT | CTGAGCGCCT | CCGAGATCTC | 1080 |
| CATCAAAGCT | GGAAGACCAA | GGACTCTAAA | CAGTGCTCAG | ACAATGTCCA | TATTTCCAGT | 1140 |
| TGACTAACCC | TGGGGTAAAG | GGTGTGTAGC | ATACGTGTAG | CTCAAGGTTA | AAAGCCATGT | 1200 |
| GTAACCAAGT | GTGCTCTTCT | TTAAGGGTTA | GTCGTAAAAG | TCAGAAGCGT | GTACTGCTAG | 1260 |
| TTCTTCAGGA | TATGCTCTTA | GGCCAGTGAC | CACTGTCATG | GATTTCAAGA | AAATCCTTGT | 1320 |
| TGACGTGTGG | ACATCAGCAG | AACTCTGGTA | TGGTTCTTAA | CTGTTACACT | GTGTTTCTGA | 1380 |
| GACCTTTCAT | GGGGCAGATA | TGTTTGTAGG | TTATCTTCTT | AAAACCCTCA | GTACAAGTTC | 1440 |
| TGGCTTACAA | AATGTACGTA | AACCTTCAAA | ACAAGTTTAC | ACTCCATATG | GCATTGATAA | 1500 |
| TCTTCAGGTG | AGCATTTAAC | GATCACTTAA | AAATCGCTAC | TGCTGATGGG | AAGAAATTTG | 1560 |

TTTATCCG                                                                                                      1568

( 2 ) INFORMATION FOR SEQ ID NO:2:

( i ) SEQUENCE CHARACTERISTICS:
        ( A ) LENGTH: 377 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

| Met | Ala | Ala | Thr | Glu | Asp | Asp | Arg | Leu | Ala | Gly | Ser | Gly | Glu | Gly | Glu |
|---|---|---|---|---|---|---|---|---|---|---|---|---|---|---|---|
| 1 | | | | 5 | | | | | 10 | | | | | 15 | |
| Arg | Leu | Asp | Phe | Leu | Arg | Asp | Arg | His | Val | Arg | Phe | Phe | Gln | Arg | Cys |
| | | | 20 | | | | 25 | | | | | | 30 | | |
| Leu | Gln | Val | Leu | Pro | Glu | Arg | Tyr | Ser | Ser | Leu | Glu | Thr | Ser | Arg | Leu |
| | | 35 | | | | | 40 | | | | | 45 | | | |
| Thr | Ile | Ala | Phe | Phe | Ala | Leu | Ser | Gly | Leu | Asp | Met | Leu | Asp | Ser | Leu |
| | | 50 | | | | | 55 | | | | | 60 | | | |
| Asp | Val | Val | Asn | Lys | Asp | Asp | Ile | Ile | Glu | Trp | Ile | Tyr | Ser | Leu | Gln |
| 65 | | | | | 70 | | | | | 75 | | | | | 80 |
| Val | Leu | Pro | Thr | Glu | Asp | Arg | Ser | Asn | Leu | Asp | Arg | Cys | Gly | Phe | Arg |
| | | | | 85 | | | | | 90 | | | | | 95 | |
| Gly | Ser | Ser | Tyr | Leu | Gly | Ile | Pro | Phe | Asn | Pro | Ser | Lys | Asn | Pro | Gly |
| | | | | 100 | | | | | 105 | | | | | 110 | |
| Thr | Ala | His | Pro | Tyr | Asp | Ser | Gly | His | Ile | Ala | Met | Thr | Tyr | Thr | Gly |
| | | | 115 | | | | | 120 | | | | | 125 | | |
| Leu | Ser | Cys | Leu | Ile | Ile | Leu | Gly | Asp | Asp | Leu | Ser | Arg | Val | Asp | Lys |
| | | 130 | | | | | 135 | | | | | 140 | | | |
| Glu | Ala | Cys | Leu | Ala | Gly | Leu | Arg | Ala | Leu | Gln | Leu | Glu | Asp | Gly | Ser |
| 145 | | | | | 150 | | | | | 155 | | | | | 160 |
| Phe | Cys | Ala | Val | Pro | Glu | Gly | Ser | Glu | Asn | Asp | Met | Arg | Phe | Val | Tyr |
| | | | | 165 | | | | | 170 | | | | | 175 | |
| Cys | Ala | Ser | Cys | Ile | Cys | Tyr | Met | Leu | Asn | Asn | Trp | Ser | Gly | Met | Asp |
| | | | 180 | | | | | 185 | | | | | 190 | | |
| Met | Lys | Lys | Ala | Ile | Ser | Tyr | Ile | Arg | Arg | Ser | Met | Ser | Tyr | Asp | Asn |
| | | 195 | | | | | 200 | | | | | 205 | | | |
| Gly | Leu | Ala | Gln | Gly | Ala | Gly | Leu | Glu | Ser | His | Gly | Gly | Ser | Thr | Phe |
| | | 210 | | | | | 215 | | | | | 220 | | | |
| Cys | Gly | Ile | Ala | Ser | Leu | Cys | Leu | Met | Gly | Lys | Leu | Glu | Glu | Val | Phe |
| 225 | | | | | 230 | | | | | 235 | | | | | 240 |
| Ser | Glu | Lys | Glu | Leu | Asn | Arg | Ile | Lys | Arg | Trp | Cys | Ile | Met | Arg | Gln |
| | | | | 245 | | | | | 250 | | | | | 255 | |
| Gln | Asn | Gly | Tyr | His | Gly | Arg | Pro | Asn | Lys | Pro | Val | Asp | Thr | Cys | Tyr |
| | | | 260 | | | | | 265 | | | | | 270 | | |
| Ser | Phe | Trp | Val | Gly | Ala | Thr | Leu | Lys | Leu | Leu | Lys | Ile | Phe | Gln | Tyr |
| | | 275 | | | | | 280 | | | | | 285 | | | |
| Thr | Asn | Phe | Glu | Lys | Asn | Arg | Asn | Tyr | Ile | Leu | Ser | Thr | Gln | Asp | Arg |
| | | 290 | | | | | 295 | | | | | 300 | | | |
| Leu | Val | Gly | Gly | Phe | Ala | Lys | Trp | Pro | Asp | Ser | His | Pro | Asp | Ala | Leu |
| 305 | | | | | 310 | | | | | 315 | | | | | 320 |
| His | Ala | Tyr | Phe | Gly | Ile | Cys | Gly | Leu | Ser | Leu | Met | Glu | Glu | Ser | Gly |
| | | | | 325 | | | | | 330 | | | | | 335 | |
| Ile | Cys | Lys | Val | His | Pro | Ala | Leu | Asn | Val | Ser | Thr | Arg | Thr | Ser | Glu |
| | | | 340 | | | | | 345 | | | | | 350 | | |

| Arg | Leu | Arg | Asp | Leu | His | Gln | Ser | Trp | Lys | Thr | Lys | Asp | Ser | Lys | Gln |
|---|---|---|---|---|---|---|---|---|---|---|---|---|---|---|---|
| | | 355 | | | | | 360 | | | | | 365 | | | |

| Cys | Ser | Asp | Asn | Val | His | Ile | Ser | Ser |
|---|---|---|---|---|---|---|---|---|
| | 370 | | | | | 375 | | |

( 2 ) INFORMATION FOR SEQ ID NO:3:

( i ) SEQUENCE CHARACTERISTICS:
      ( A ) LENGTH: 1969 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:3:

```
GAATAAAATG AACAATTCAG TTCCTCAGTC ACATGAGCTG TGTGTCAAAT GCACAACAGC      60
CGTATGTGGC TCGTGGCCCC TGTACCGGAC ACTCCATCC  CTGCAGAGTT ACTGGACAGT     120
GCTGATCTAG GGATTCTGTT ACAAAATCCA TGAAAGTGTT CAGCACAATG CCGGGCCCAT     180
ATAAACGTCA GTAGTTGTTG TTATTATAAT TAGTCTTGAC CCAACGGCAA ATTCACTTTG     240
AGACCTTAGA TAAATCACTC TACCTCTCTG AGCCTGGTTT CCTTGCCCTA AAAGGATGGC     300
AAGGGGCTGG GCATGGTGGC CACTGAGGAT GAGAGGCTAG CAGGGAGCGG TGAGGGAGAG     360
CGGCTGGATT TCTTACGGGA TCGGCACGTG CGATTTTCC  AGCGCTGCCT CCAGGTTTTG     420
CCGGAGCGCT ATTCTTCACT CGAGACAAGC AGGTTGACAA TTGCATTTTT TGCACTCTCC     480
GGGCTGGATA TGTTGGATTC CTTAGATGTG GTGAACAAAG ATGATATAAT AGAGTGGATT     540
TATTCCCTGC AGGTCCTTCC CACAGAAGAC AGATCAAATC TAAATCGCTG TGGTTTCCGA     600
GGCTCTTCAT ACCTGGGTAT TCCGTTCAAT CCATCAAAGG CTCCTGGAAC AGCTCATCCT     660
TATGATAGTG GCCACATTGC AATGACCTAC ACTGGCCTCT CATGCTTAGT TATTCTTGGA     720
GACGACTTAA GCCGAGTAAA TAAAGAAGCT TGCTTAGCGG GCTTGAGAGC CCTTCAGCTG     780
GAAGATGGGA GTTTTGTGC  AGTACCTGAA GGCAGTGAAA ATGACATGCG ATTTGTGTAC     840
TGTGCTTCCT GTATTTGCTA TATGCTCAAC AACTGGTCAG GCATGGATAT GAAAAAAGCC     900
ATCACCTATA TTAGAAGGAG TATGTCCTAT GACAATGGAC TGGCACAGGG AGCTGGACTT     960
GAATCTCATG GAGGATCAAC TTTTTGTGGC ATTGCCTCAC TATGTCTGAT GGGTAAACTA    1020
GAAGAAGTTT TTCAGAAAA  AGAATTGAAC AGGATAAAGA GGTGGTGTAT AATGAGGCAA    1080
CAAAATGGTT ATCATGGAAG ACCTAATAAG CCTGTAGACA CCTGTTATTC TTTTTGGGTG    1140
GGAGCAACTC TGAAGCTTCT AAAAATTTTC CAATACACTA ACTTTGAGAA AAATAGAAAT    1200
TACATCTTAT CAACTCAAGA TCGCCTTGTA GGGGGATTTG CCAAGTGGCC AGACAGTCAT    1260
CCAGATGCTT TGCATGCATA CTTTGGGATC TGTGGCCTGT CACTAATGGA GGAAAGTGGA    1320
ATTTGTAAAG TTCATCCTGC TCTGAATGTA AGCACACGGA CTTCTGAACG CCTTCTAGAT    1380
CTCCATCAAA GCTGGAAAAC CAAGGACTCT AAACAATGCT CAGAGAATGT ACATATCTCC    1440
ACATGACTGA TTTTAGATTG GGAGGGTGGG GGGGATTTGT AGCATAACTG TAGCTCAAGT    1500
TTAAAAGCCA TGTATAACCA AGTGTGCTCT TTTTTTAAAA GGTAGAGTCT TACAATCAAA    1560
TCTCCTGCTG ATTTCACTTT GGGATATGGT CTTGAGCCAG TAATCTTTAT ACTGGGTTTC    1620
AAGAAAATCT TTGTTGAAGT TTGAACCACA ACTTTGTCGT GGTTCTTAAA TGTTTATACT    1680
GTATTTCTAA GAAGTTGTTT GAGGCAAATT AACTGTATGT GTGTAGGTTA TCTTTTTAAA    1740
AACTCTTCAG TGCAAATTGT ATCTTATTAT AAAATGGACA CAAATTTTCA AGTTTACACT    1800
```

```
TCATATAGCA TTGATAATCT TCAGGTGAAC ACTTAGTGAT CATTTAAAAA GCTCACTGCT    1860

GATCGTAGAA AATTTGCTTT AATTAATTAA GTATCTGGGA TTATTCTTTG AAAACAGATG    1920

ACCATAATTT TTTTTAAAGA AGAGTGACTT ATTTGTCTT ATTCTTAAG                 1969
```

( 2 ) INFORMATION FOR SEQ ID NO:4:

( i ) SEQUENCE CHARACTERISTICS:
        ( A ) LENGTH: 377 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Met Val Ala Thr Glu Asp Glu Arg Leu Ala Gly Ser Gly Glu Gly Glu
 1               5                  10                  15

Arg Leu Asp Phe Leu Arg Asp Arg His Val Arg Phe Phe Gln Arg Cys
             20                  25                  30

Leu Gln Val Leu Pro Glu Arg Tyr Ser Ser Leu Glu Thr Ser Arg Leu
         35                  40                  45

Thr Ile Ala Phe Phe Ala Leu Ser Gly Leu Asp Met Leu Asp Ser Leu
     50                  55                  60

Asp Val Val Asn Lys Asp Asp Ile Ile Glu Trp Ile Tyr Ser Leu Gln
 65                  70                  75                  80

Val Leu Pro Thr Glu Asp Arg Ser Asn Leu Asn Arg Cys Gly Phe Arg
                 85                  90                  95

Gly Ser Ser Tyr Leu Gly Ile Pro Phe Asn Pro Ser Lys Ala Pro Gly
            100                 105                 110

Thr Ala His Pro Tyr Asp Ser Gly His Ile Ala Met Thr Tyr Thr Gly
        115                 120                 125

Leu Ser Cys Leu Val Ile Leu Gly Asp Asp Leu Ser Arg Val Asn Lys
    130                 135                 140

Glu Ala Cys Leu Ala Gly Leu Arg Ala Leu Gln Leu Glu Asp Gly Ser
145                 150                 155                 160

Phe Cys Ala Val Pro Glu Gly Ser Glu Asn Asp Met Arg Phe Val Tyr
                165                 170                 175

Cys Ala Ser Cys Ile Cys Tyr Met Leu Asn Asn Trp Ser Gly Met Asp
            180                 185                 190

Met Lys Lys Ala Ile Thr Tyr Ile Arg Arg Ser Met Ser Tyr Asp Asn
        195                 200                 205

Gly Leu Ala Gln Gly Ala Gly Leu Glu Ser His Gly Gly Ser Thr Phe
    210                 215                 220

Cys Gly Ile Ala Ser Leu Cys Leu Met Gly Lys Leu Glu Glu Val Phe
225                 230                 235                 240

Ser Glu Lys Glu Leu Asn Arg Ile Lys Arg Trp Cys Ile Met Arg Gln
                245                 250                 255

Gln Asn Gly Tyr His Gly Arg Pro Asn Lys Pro Val Asp Thr Cys Tyr
            260                 265                 270

Ser Phe Trp Val Gly Ala Thr Leu Lys Leu Leu Lys Ile Phe Gln Tyr
        275                 280                 285

Thr Asn Phe Glu Lys Asn Arg Asn Tyr Ile Leu Ser Thr Gln Asp Arg
    290                 295                 300

Leu Val Gly Gly Phe Ala Lys Trp Pro Asp Ser His Pro Asp Ala Leu
305                 310                 315                 320

His Ala Tyr Phe Gly Ile Cys Gly Leu Ser Leu Met Glu Glu Ser Gly
```

|   |   |   |   |   | 325 |   |   |   |   | 330 |   |   |   |   | 335 |   |   |
|---|---|---|---|---|---|---|---|---|---|---|---|---|---|---|---|---|---|
| Ile | Cys | Lys | Val | His | Pro | Ala | Leu | Asn | Val | Ser | Thr | Arg | Thr | Ser | Glu |
|   |   |   | 340 |   |   |   |   | 345 |   |   |   |   | 350 |   |   |
| Arg | Leu | Leu | Asp | Leu | His | Gln | Ser | Trp | Lys | Thr | Lys | Asp | Ser | Lys | Gln |
|   |   | 355 |   |   |   |   | 360 |   |   |   |   | 365 |   |   |   |
| Cys | Ser | Glu | Asn | Val | His | Ile | Ser | Thr |
|   |   | 370 |   |   |   | 375 |   |   |

( 2 ) INFORMATION FOR SEQ ID NO:5:

( i ) SEQUENCE CHARACTERISTICS:
( A ) LENGTH: 1670 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

```
GGATCCAGTA CTTATGGTAG CCACTGAGGA TGAGAGGCTA GCAGGGAGCG GTGAGGGAGA      60
GCGGCTGGAT TTCTTACGGG ATCGGCACGT GCGATTTTTC CAGCGCTGCC TCCAGGTTTT     120
GCCGGAGCGC TATTCTTCAC TCGAGACAAG CAGGTTGACA ATTGCATTTT TTGCACTCTC     180
CGGGCTGGAT ATGTTGGATT CCTTAGATGT GGTGAACAAA GATGATATAA TAGAGTGGAT     240
TTATTCCCTG CAGGTCCTTC CCACAGAAGA CAGATCAAAT CTAAATCGCT GTGGTTTCCG     300
AGGCTCTTCA TACCTGGGTA TTCCGTTCAA TCCATCAAAG GCTCCTGGAA CAGCTCATCC     360
TTATGATAGT GGCCACATTG CAATGACCTA CACTGGCCTC TCATGCTTAG TTATTCTTGG     420
AGACGACTTA AGCCGAGTAA ATAAGAAGC TTGCTTAGCG GGCTTGAGAG CCCTTCAGCT     480
GGAAGATGGG AGTTTTGTG CAGTACCTGA AGGCAGTGAA AATGACATGC GATTTGTGTA     540
CTGTGCTTCC TGTATTTGCT ATATGCTCAA CAACTGGTCA GGCATGGATA TGAAAAAAGC     600
CATCACCTAT ATTAGAAGGA GTATGTCCTA TGACAATGGA CTGGCACAGG GAGCTGGACT     660
TGAATCTCAT GGAGGATCAA CTTTTTGTGG CATTGCCTCA CTATGTCTGA TGGGTAAACT     720
AGAAGAAGTT TTTTCAGAAA AAGAATTGAA CAGGATAAAG AGGTGGTGTA TAATGAGGCA     780
ACAAAATGGT TATCATGGAA GACCTAATAA GCCTGTAGAC ACCTGTTATT CTTTTGGGT     840
GGGAGCAACT CTGAAGCTTC TAAAAATTTT CCAATACACT AACTTTGAGA AAAATAGAAA     900
TTACATCTTA TCAACTCAAG ATCGCCTTGT AGGGGGATTT GCCAAGTGGC CAGACAGTCA     960
TCCAGATGCT TTGCATGCAT ACTTTGGGAT CTGTGGCCTG TCACTAATGG AGGAAAGTGG    1020
AATTTGTAAA GTTCATCCTG CTCTGAATGT AAGCACACGG ACTTCTGAAC GCCTTCTAGA    1080
TCTCCATCAA AGCTGGAAAA CCAAGGACTC TAAACAATGC TCAGAGAATG TACATATCTC    1140
CACATGACTG ATTTAGATT GGGAGGGTGG GGGGATTTG TAGCATAACT GTAGCTCAAG    1200
TTTAAAAGCC ATGTATAACC AAGTGTGCTC TTTTTTTAAA AGGTAGAGTC TTACAATCAA    1260
ATCTCCTGCT GATTTCACTT TGGGATATGG TCTTGAGCCA GTAATCTTTA TACTGGGTTT    1320
CAAGAAAATC TTTGTTGAAG TTTGAACCAC AACTTTGTCG TGGTTCTTAA ATGTTATAC    1380
TGTATTTCTA AGAAGTTGTT TGAGGCAAAT TAACTGTATG TGTGTAGGTT ATCTTTTTAA    1440
AAACTCTTCA GTGCAAATTG TATCTTATTA TAAAATGGAC ACAAATTTTC AAGTTACAC    1500
TTCATATAGC ATTGATAATC TTCAGGTGAA CACTTAGTGA TCATTTAAAA AGCTCACTGC    1560
TGATCGTAGA AAATTTGCTT TAATTAATTA AGTATCTGGG ATTATTCTTT GAAAACAGAT    1620
GACCATAATT TTTTTTAAAG AAGAGTGACT TATTTTGTCT TATTCTTAAG               1670
```

( 2 ) INFORMATION FOR SEQ ID NO:6:

( i ) SEQUENCE CHARACTERISTICS:
        ( A ) LENGTH: 2913 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
GGATCCATTG  GAGGATGATT  AAATGGCTGC  TACTGAAGGT  GTTGGTGAAG  CTGCACAGGG    60
TGGTGAGCCC  GGGCAGCCGG  CGCAACCCCC  GCCCCAGCCG  CACCCACCGC  CGCCCCAGCA   120
GCAGCACAAG  GAAGAGATGG  CGGCCGAGGC  TGGGGAAGCC  GTGGCGTCCC  CCATGGACGA   180
CGGGTTTGTG  AGCCTGGACT  CGCCCTCCTA  TGTCCTGTAC  AGGGACAGAG  CAGAATGGGC   240
TGATATAGAT  CCGGTGCCGC  AGAATGATGG  CCCCAATCCC  GTGGTCCAGA  TCATTTATAG   300
TGACAAATTT  AGAGATGTTT  ATGATTACTT  CCGAGCTGTC  CTGCAGCGTG  ATGAAAGAAG   360
TGAACGAGCT  TTTAAGCTAA  CCCGGGATGC  TATTGAGTTA  AATGCAGCCA  ATTATACAGT   420
GTGGCATTTC  CGGAGAGTTC  TTTTGAAGTC  ACTTCAGAAG  GATCTACATG  AGGAAATGAA   480
CTACATCACT  GCAATAATTG  AGGAGCAGCC  CAAAAACTAT  CAAGTTTGGC  ATCATAGGCG   540
AGTATTAGTG  GAATGGCTAA  GAGATCCATC  TCAGGAGCTT  GAATTTATTG  CTGATATTCT   600
TAATCAGGAT  GCAAAGAATT  ATCATGCCTG  GCAGCATCGA  CAATGGGTTA  TTCAGGAATT   660
TAAACTTTGG  GATAATGAGC  TGCAGTATGT  GGACCAACTT  CTGAAAGAGG  ATGTGAGAAA   720
TAACTCTGTC  TGGAACCAAA  GATACTTCGT  TATTTCTAAC  ACCACTGGCT  ACAATGATCG   780
TGCTGTATTG  GAGAGAGAAG  TCCAATACAC  TCTGGAAATG  ATTAAACTAG  TACCACATAA   840
TGAAAGTGCA  TGGAACTATT  TGAAAGGGAT  TTTGCAGGAT  CGTGGTCTTT  CCAAATATCC   900
TAATCTGTTA  AATCAATTAC  TTGATTTACA  ACCAAGTCAT  AGTTCCCCCT  ACCTAATTGC   960
CTTTCTTGTG  GATATCTATG  AAGACATGCT  AGAAAATCAG  TGTGACAATA  AGGAAGACAT  1020
TCTTAATAAA  GCATTAGAGT  TATGTGAAAT  CCTAGCTAAA  GAAAAGGACA  CTATAAGAAA  1080
GGAATATTGG  AGATACATTG  GAAGATCCCT  TCAAAGCAAA  CACAGCACAG  AAAATGACTC  1140
ACCAACAAAT  GTACAGCAAT  AAGAATTAAT  TCGGTACCCG  GGATCCTCT   AGAGTCGAGG  1200
AGTTTTAAAC  TTATGGTAGC  CACTGAGGAT  GAGAGGCTAG  CAGGGAGCGG  TGAGGGAGAG  1260
CGGCTGGATT  TCTTACGGGA  TCGGCACGTG  CGATTTTCC   AGCGCTGCCT  CCAGGTTTTG  1320
CCGGAGCGCT  ATTCTTCACT  CGAGACAAGC  AGGTTGACAA  TTGCATTTTT  TGCACTCTCC  1380
GGGCTGGATA  TGTTGGATTC  CTTAGATGTG  GTGAACAAAG  ATGATATAAT  AGAGTGGATT  1440
TATTCCCTGC  AGGTCCTTCC  CACAGAAGAC  AGATCAAATC  TAAATCGCTG  TGGTTTCCGA  1500
GGCTCTTCAT  ACCTGGGTAT  TCCGTTCAAT  CCATCAAAGG  CTCCTGGAAC  AGCTCATCCT  1560
TATGATAGTG  CCACATTGC   AATGACCTAC  ACTGGCCTCT  CATGCTTAGT  TATTCTTGGA  1620
GACGACTTAA  GCCGAGTAAA  TAAAGAAGCT  TGCTTAGCGG  GCTTGAGAGC  CCTTCAGCTG  1680
GAAGATGGGA  GTTTTGTGC   AGTACCTGAA  GGCAGTGAAA  ATGACATGCG  ATTTGTGTAC  1740
TGTGCTTCCT  GTATTTGCTA  TATGCTCAAC  AACTGGTCAG  GCATGGATAT  GAAAAAAGCC  1800
ATCACCTATA  TTAGAAGGAG  TATGTCCTAT  GACAATGGAC  TGGCACAGGG  AGCTGGACTT  1860
GAATCTCATG  GAGGATCAAC  TTTTTGTGGC  ATTGCCTCAC  TATGTCTGAT  GGGTAAACTA  1920
GAAGAAGTTT  TTCAGAAAA   AGAATTGAAC  AGGATAAAGA  GGTGGTGTAT  AATGAGGCAA  1980
CAAAATGGTT  ATCATGGAAG  ACCTAATAAG  CCTGTAGACA  CCTGTTATTC  TTTTGGGTG   2040
```

```
GGAGCAACTC  TGAAGCTTCT  AAAAATTTTC  CAATACACTA  ACTTTGAGAA  AAATAGAAAT    2100

TACATCTTAT  CAACTCAAGA  TCGCCTTGTA  GGGGGATTTG  CCAAGTGGCC  AGACAGTCAT    2160

CCAGATGCTT  TGCATGCATA  CTTTGGGATC  TGTGGCCTGT  CACTAATGGA  GGAAAGTGGA    2220

ATTTGTAAAG  TTCATCCTGC  TCTGAATGTA  AGCACACGGA  CTTCTGAACG  CCTTCTAGAT    2280

CTCCATCAAA  GCTGGAAAAC  CAAGGACTCT  AAACAATGCT  CAGAGAATGT  ACATATCTCC    2340

ACATGACTGA  TTTAGATTG   GGAGGGTGGG  GGGGATTTGT  AGCATAACTG  TAGCTCAAGT    2400

TTAAAAGCCA  TGTATAACCA  AGTGTGCTCT  TTTTTAAAA   GGTAGAGTCT  TACAATCAAA    2460

TCTCCTGCTG  ATTTCACTTT  GGGATATGGT  CTTGAGCCAG  TAATCTTTAT  ACTGGGTTTC    2520

AAGAAAATCT  TTGTTGAAGT  TTGAACCACA  ACTTTGTCGT  GGTTCTTAAA  TGTTTATACT    2580

GTATTTCTAA  GAAGTTGTTT  GAGGCAAATT  AACTGTATGT  GTGTAGGTTA  TCTTTTAAA    2640

AACTCTTCAG  TGCAAATTGT  ATCTTATTAT  AAAATGGACA  CAAATTTTCA  AGTTTACACT    2700

TCATATAGCA  TTGATAATCT  TCAGGTGAAC  ACTTAGTGAT  CATTTAAAAA  GCTCACTGCT    2760

GATCGTAGAA  AATTTGCTTT  AATTAATTAA  GTATCTGGGA  TTATTCTTTG  AAAACAGATG    2820

ACCATAATTT  TTTTTAAAGA  AGAGTGACTT  ATTTTGTCTT  ATTCTTAAGG  AATTCCTGCA    2880

GCCCGGGGGA  TCCGTCGACC  TGCAGCCAAG  CTT                                  2913
```

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Phe  Gln  Asp  Val  Tyr  Asp  Tyr  Phe  Arg
1                  5
```

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Gln  Trp  Val  Ile  Gln  Glu  Phe  Lys
1                  5
```

( 2 ) INFORMATION FOR SEQ ID NO:9:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Val  Leu  Val  Glu  Trp  Leu  Arg  Asp  Pro  Ser  Gln  Glu  Leu  Glu  Phe  Ile
1                  5                            10                           15

Ala  Asp  Ile  Leu  Thr  Gln  Asp  Ala  Lys
```

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Thr Ile Ala Phe Phe Ala Leu Ser Gly Leu Asp Met Leu Asp
1               5                   10
```

(2) INFORMATION FOR SEQ ID NO:11:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Gly Ser Ser Tyr Leu Gly Ile Pro Phe Asn Pro Ser Lys
1               5                   10
```

(2) INFORMATION FOR SEQ ID NO:12:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Ile Phe Gln Tyr Thr Asn Phe Glu Lys
1               5
```

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Asn Tyr Ile Leu Ser Thr Gln Asp Arg
1               5
```

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Asp Leu His Gln Ser Trp Lys
```

(2) INFORMATION FOR SEQ ID NO:15:

(i) SEQUENCE CHARACTERISTICS:
　　　　(A) LENGTH: 28 base pairs
　　　　(B) TYPE: nucleic acid
　　　　(C) STRANDEDNESS: single
　　　　(D) TOPOLOGY: linear (ii) MOLECULE TYPE: DNA (genomic)

(xi) SEQUENCE DESCRIPTION: SEQ ID NO:15:

GCTCGGATCC CRAARTTNGT RTAYTGRA　　　　　　　　　　　　　　　　　　　　　28

(2) INFORMATION FOR SEQ ID NO:16:

(i) SEQUENCE CHARACTERISTICS:
　　　　(A) LENGTH: 27 base pairs
　　　　(B) TYPE: nucleic acid
　　　　(C) STRANDEDNESS: single
　　　　(D) TOPOLOGY: linear (ii) MOLECULE TYPE: DNA (genomic)

(xi) SEQUENCE DESCRIPTION: SEQ ID NO:16:

GTCGGAATTC ACNATHGCNT TYTTYGC　　　　　　　　　　　　　　　　　　　　　27

(2) INFORMATION FOR SEQ ID NO:17:

(i) SEQUENCE CHARACTERISTICS:
　　　　(A) LENGTH: 27 base pairs
　　　　(B) TYPE: nucleic acid
　　　　(C) STRANDEDNESS: single
　　　　(D) TOPOLOGY: linear (ii) MOLECULE TYPE: DNA (genomic)

(xi) SEQUENCE DESCRIPTION: SEQ ID NO:17:

GTACTCTAGA GGNATHCCNT TYAAYCC　　　　　　　　　　　　　　　　　　　　　27

(2) INFORMATION FOR SEQ ID NO:18:

(i) SEQUENCE CHARACTERISTICS:
　　　　(A) LENGTH: 24 base pairs
　　　　(B) TYPE: nucleic acid
　　　　(C) STRANDEDNESS: single
　　　　(D) TOPOLOGY: linear (ii) MOLECULE TYPE: DNA (genomic)

(xi) SEQUENCE DESCRIPTION: SEQ ID NO:18:

GAATTCATGN TAAGAATTAA TTCN　　　　　　　　　　　　　　　　　　　　　　24

(2) INFORMATION FOR SEQ ID NO:19:

(i) SEQUENCE CHARACTERISTICS:
　　　　(A) LENGTH: 70 base pairs
　　　　(B) TYPE: nucleic acid
　　　　(C) STRANDEDNESS: single
　　　　(D) TOPOLOGY: linear (ii) MOLECULE TYPE: DNA (genomic)

(xi) SEQUENCE DESCRIPTION: SEQ ID NO:19:

GAATTCTAGA TATATGGCTG CTACTGAAGG TGTTGGTGAA GCTGCACAGG GTGGTNTAAG　　　　60

AATTAATTCN　　　　　　　　　　　　　　　　　　　　　　　　　　　　　　70

( 2 ) INFORMATION FOR SEQ ID NO:20:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

```
Met Ala Ala Thr Glu Gly Val Gly Glu Ala Ala Gln Gly Gly
  1               5                  10
```

( 2 ) INFORMATION FOR SEQ ID NO:21:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

```
GGATCCATTG GAGGATGATT AAATGGCTGC TACTGAAGGT GTTGGTGAAG CTGCACAGGG    60

TGGTGAGCCC NGAGGAGTTT TAATTAAGAA TTCN                               94
```

( 2 ) INFORMATION FOR SEQ ID NO:22:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Asp Pro Leu Glu Asp Asp
  1               5
```

( 2 ) INFORMATION FOR SEQ ID NO:23:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
NGAGGAGTTT TAACTTATGG TAN                                           23
```

( 2 ) INFORMATION FOR SEQ ID NO:24:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

```
Cys Gly Ser Ser Tyr Leu Gly Ile Pro Phe Asn Pro Ser Lys
  1               5                  10
```

(2) INFORMATION FOR SEQ ID NO:25:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Ile Gly Arg Ser Leu Gln Ser Lys His Ser Thr Glu Cys
 1               5                  10
```

(2) INFORMATION FOR SEQ ID NO:26:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
ACGATAGCGT TTTTTGCACT CTCCGGGCTG GATATGTTGG ATTCCTTAGA TGTGGTGAAC      60
AAAGATGATA TAATAGAGTG GATTTATTGG GTGCAGGTCC TTCCCACAGA AGACAGATCA     120
AATCTAAATC GCTGTGGTTT CCGAGGCTCT TCATACCTGG GTATTCCGTT CAATCCATCA     180
AAGGCTCCTG GAACAGCTCA TCCTTATGAT AGTGGCCACA TTGCAATGAC CTACACTGGC     240
CTCTCATGCT TAGTTATTCT TGGAGACGAC TTAAGCCGAG TAAATAAAGA AGCTTGCTTA     300
GCGGGCTTGA GAGCCCTTCA GCTGGAAGAT GGGAGTTTTT GTGCAGTACC TGAAGGCAGT     360
GAAAATGACA TGCGATTTGT GTACTGTGCT TCCTGTATTT GCTATATGCT CAACAACTGG     420
TCAGGCATGG ATATGAAAAA GCCATCACCT ATATTAGAAG GAGTATGTCC TATGACAATG     480
GACTGGCACA GGGAGCTGGA CTTGAATCTC ATGGAGGATC AACTTTTTGT GGCATTGCCT     540
CACTATGTCT GATGGGTAAA CTAGAAGAAG TTTTTTCAGA AAAAGAATTG AACAGGATAA     600
AGAGGTGGTG TATAATGAGG CAACAAAATG GTTATCATGG AAGACCTAAT AAGCCTGTAG     660
ACACCTGTTA TTCTTTTTGG GTGGGAGCAA CTCTGAAGCT TCTAAAAATT TTCCAATACA     720
CCAACTTCG                                                            729
```

(2) INFORMATION FOR SEQ ID NO:27:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Met Ala Ala Thr Glu Gly Val Gly Glu Ala Ala Gln Gly Gly Glu Pro
 1               5                  10                  15
```

What is claimed is:

1. An isolated nucleic acid encoding geranylgeranyltransferase type I (GGTase-I) wherein a β subunit of said GGTase-I has the amino acid sequence set forth in SEQ.ID NO:2 or SEQ.ID NO:4.

2. An isolated nucleic acid encoding the α subunit of mammalian GGTase-I wherein the nucleic acid encodes the amino acid sequence set forth in SEQ.ID NO:2 or SEQ.ID NO:4.

3. The isolated nucleic acid according to claim 2 wherein the nucleic acid has the sequence shown in SEQ.ID NO:1 or SEQ.ID NO:3 or a sequence substantially identical thereto.

* * * * *